United States Patent [19]
Briles et al.

[11] Patent Number: 6,042,838
[45] Date of Patent: Mar. 28, 2000

[54] IMMUNOGENIC COMPOSITIONS FOR MUCOSAL ADMINISTRATION OF PNEUMOCOCCAL SURFACE PROTEIN A (PSPA)

[75] Inventors: David E. Briles; Hong-Yin Wu, both of Birmingham, Ala.

[73] Assignee: UAB Research Foundation, Birmingham, Ala.

[21] Appl. No.: 08/446,201

[22] Filed: May 19, 1995

Related U.S. Application Data

[63] Continuation-in-part of application No. 08/312,949, Sep. 30, 1994, which is a continuation-in-part of application No. 08/246,636, May 20, 1994, which is a continuation-in-part of application No. 08/048,896, Apr. 20, 1993, abandoned, which is a continuation-in-part of application No. 07/835, 698, Feb. 12, 1992, abandoned, which is a continuation-in-part of application No. 07/656,773, Feb. 15, 1991, abandoned.

[51] Int. Cl.$^7$ .......................... A61K 39/09; A61K 39/00; C12P 21/06
[52] U.S. Cl. ..................... 424/244.1; 424/184.1; 424/237.1; 435/69.1
[58] Field of Search ............................. 424/244.1, 184.1, 424/183.1, 237.1, 93.3, 93.43; 435/69.1

[56] References Cited

U.S. PATENT DOCUMENTS

| | | | |
|---|---|---|---|
| 4,873,890 | 10/1989 | Clancey et al. | |
| 5,182,109 | 1/1993 | Tamura et al. | 424/92 |
| 5,476,929 | 12/1995 | Briles et al. | 536/24.32 |

FOREIGN PATENT DOCUMENTS

| | | | |
|---|---|---|---|
| 303804 | 5/1991 | WIPO | |
| 214488 | 9/1991 | WIPO | A61K 39/02 |

OTHER PUBLICATIONS

Bixten et al. Synthetic Vaccines, vol. 1, pp. 39–71, 1987.
Van de Wiggert et al, Infection and Immunity, 59:2750–57, 1991.
Fontanges et al. Rev. Fr. Allergol 17: 35–41, 1977 Abstract only.
Garcia et al. FTMS Microbiol Lett. 108:163–167, 1993, Abstract only.
Kurl et al., Acta Path Microbiol Immunol. 93: 401–405, 1985 Abstract only.
McDaniel et al., Infect & Immunity 59: 222–228, 1991.
Talkington et al. Infection & Immunity 59: 1285–1289, 1991.
Germie et al., Novel Vaccine Strategies: Mucosal Immunization, Adjuvants and Genetic Approaches Oct. 1993, Abstract only.
Bessen et al. Joun. of Immunology 1990, vol. 145: 1251–1256.
Wu et al. Infection & Immunity 61: 314–327, 1993.
Anonymous. Centers for Disease Control HIV/AIDS Surveillance Report. 1991; Aug.: 1–18.

Fraser DW. What Are Our Bacterial Disease Problems. In: JB Robbins, Hill JC, Sadoff JC ed. Bacterial Vaccines. New York: 1982: xix–xxiv.

Berman S, McIntosh K. Selective Primary Health Care: Strategies For Control Of Disease In The Developing World. XXI Acute Respiratory Infections. Rev. Infect. Dis. 1985; 7:647–491.

Greenwood BM, Greenwood AM, Bradley AK, Tulloch S, Hayes R, Oldfield FSJ. Deaths In Infancy And Early Childhood In A Well Vaccinated, Rural, West African Population. Ann. Trop. Pediatr. 1987; 7:91–99.

Spika JS, Munshi MH, Wojtyaniak B, Sack DA, Hossain A., Rahman M, Saha SK, Acute Lower Respiratory Infections: A Major Cause Of Death In Children In Bangladesh. Ann. Trop. Pediatr. 1989; 9: 33–39.

Bale JR, Etiology And Epidemiology Of Acute Respiratory Tract Infections In Children In Developing Countries. Rev. Infect. Dis. 1990; 12 (Suppl. 8): S861–S1083.

Munoz R, Musser JM, Crain M, Briles DE, Marton A, Parkinson AJ, Sorensen U, Tomasz A. Geographic Distribution Of Penicillin–Resistant Clones Of *Streptococcus Pneumoniae*: Characterization By Penicillin–Binding Protein Profile, Surface Protein A Typing, and Multilocus Enzyme Analysis. Clinic. Infect. Dis. 1992; 15:112–118.

Marton A, Gulyas M, Munoz R, Tomasz A. Extremely High Incidence Of Antibiotic Resistance In Clinical Isolates Of *Streptococcus Pneumoniae*: In Hungary. J. Infect. Dis. 1991; 163: 542–548.

Klugman KP. Pneumococcal Resistance To Antibiotics. Clin. Microbiol. Rev. 1990.

Gray BM, Converse GM III, Dillon HC. Epidemiologic Studies Of *Streptococcus Pneumoniae* In Infants: Acquisition, Carriage, And Infection During The First 24 Months Of Life. J. Infect. Dis. 1980; 142: 923–933.

Gray BM, Converse GM III, Huhta N., Johnston RB Jr., Pichichero ME, Schiffman G. Dillon HC Jr. Antibody Response To Pneumococcal Carriage. J. Infect. Dis. 1981; 142:312–318.

Hendley JO, Sande MA, Stewart PM, et al. Spread Of *Streptococcus Peumoniae* In Families. I. Carriage Rates And Distribution Of Types. J. Infect. Dis. 1975; 132–55.

(List continued on next page.)

*Primary Examiner*—James C. Housel
*Assistant Examiner*—Rodney P. Swartz
*Attorney, Agent, or Firm*—Frommer Lawerence & Haug LLP; William S. Frommer; Thomas J. Kowalski

[57] ABSTRACT

Mucosal administration, particularly intranasally, of killed whole pneumococci, lysate of pneumococci and isolated and purified PspA, as well as immunogenic fragments thereof, particularly when administered with cholera toxin B subunit, provides protection in animals against pneumococcal colonization and systemic infection. The ability to elicit protection against pneumococcal colonization in a host prevents carriage among immunized individuals, which can lead to elimination of disease from the population as a whole.

8 Claims, 8 Drawing Sheets

OTHER PUBLICATIONS

Smillie WG, Warnock GH, White HJ. A Study Of A Type 1 Pneumococcus At State Hospital At Worchester Massachusetts. Am. J. Pub. Hlth 1938; 28: 293–302.

Smillie WG, A Study Of An Outbreak Of Type II Pneumococcal Pneumonia In The Veterans Administration Hospital At Bedford, Massachusetts, Am. J. Hyg. 1936; 24:522–535.

Gratten M, Naraqi S, Hansman D. High Prevalence Of Penicillin–Insensitive Pneumococci In Port Moresby, Paupa New Guinea. Lancet 1980; 11:192–195.

DeMaria TF, McGhee RB, Lim DJ. Rheumatoid Factor In Otitis Media With Effusion. Arch Otolaryngol. 1984; 110:279–280.

Bohr V, Rasmussen N, Hansen B, Gade A, Kjersem H, Johsen N. Paulson O. Pheumococcal meningitis: An Evaluation Of Prognostic Factors In 164 Cases Based On Mortality And On A Study Of Lasting Sequelae. J. Infect. Dis. 1985; 10:143–157.

Klein Jo. The Epidemiology Of Pneumococcal Diseases In Infants And Children. Rev. Infect. Dis. 1981; 3: 246–.

Bolan G, Broome CV, Facklam RR, Plikaytis BD, Fraser WD, Schlech WFI. Pneumococcal Vaccine Efficacy In Selected Populations In The United States. Ann. Intern. Med. 1986; 104: 1–6.

Shapiro ED, Berg AT, Austrian R, Schroeder D, Parcells, Margolis, Adair RK, Clemmens JD., Protective Efficacy Of Polyvalent Pneumococcal Polysaccharide Vaccine. N. Engl. J. Med 1991; 325: 1453–1460.

Cowan MJ, Ammann AJ, Wara DW, Howie VM, Schultz L, Doyle N, Kaplan M, Pneumococcal Polysaccharide Immunization In Infants And Children. Pediatrics 1978; 62: 721–727.

Gotschlich EC, Goldschneider I, Lepow ML, Gold R. The Immune Response To Bacterial Polysaccharides In Man. Antibodies In Human Diagnosis And Therapy. New York: Raven, 1977: 391–402.

Barbour ML, Mayon–White RT, Crook DW, Coles C, Moxon ER. The Influence Of Haemophilus Influenzae Type B (Hib) Conjugate Vaccine (PRP–T) On Oropharyngeal Carriage Of Hib In Infants Under 12 Months Of Age. ICAAC Abstracts 1993: 33:175.

Chiu SS, Greenberg PD, Marcy SM, Wong VK, Chang SJ, Chiu CY, Ward JI. Mucosal Antibody Responses In Infants Following Immunization With Haemophilus Influenzae Pediatric Res. Abstracts 1994; 35 : 10A.

Fallon MT, Reinhard MK, Gray BM, Davis TW, Lindsey JR. Inapparent *Streptococcus Pneumoniae* Yype 35 Infections In Commercial Rats And Mice. Laboratory Animal Science 1988; 38:129–.

Douglas RM, DH, Miles HB, Paton JC, Pneumococcal carriage and Type–Specific Antibody Failure Of A 14–Valent Vaccine To Reduce Carriage In Healthy Children. American Journal of Diseases of Children 1986; 140 : 1183–1185.

Douglas RM, Miles HB. Vaccination Against *Streptococcus Pneumoniae* In Childhood: Lack Of Demonstrable Benefit In Young Australian Children. Journal of Infectious Diseases 1984; 149:861–869.

Mestecky J. The Common Mucosal Immune System And Current Strategies For Induction Of Immune Response In External Secretions. J. Clin. Immunol. 1987; 7:265–276.

Croitoru K, Bienenstock J. Characteristics And Functions Of Mucosa–Associated Lymphoid Tissue. In: PL Ogra, Mestecky J, Lamm ME, Strober W, McGhee JR, Bienenstock J ed. Handbook of Mucosal Immunology. San Diego, CA: Academic Press, Inc., 1994: 141–149.

Bienenstock J, Johnston N, Perey DY. Bronchial Lymphoid Tissue. I. Morphologic Characteristics. Lab. Invest. 1973; 28: 686–692.

Bienenstock J. Johnston N. Perey DY. Bronchial Lymphoid Tissue. II. Functional Characteristics. Lab. Invest. 1973; 693–698.

Pabst R. Is BALT a Major Component Of The Human Lung Immune System? Immunology Today 1992; 13:119–122.

Kuper CF, Koomstra PJ, Hameleers DMH, Biewenga J, Spit BJ, Duijvestijn AM, van Breda Vriesman PJC, Sminia T. The Role Of Nasopharyngeal Lymphoid Tissue. Immunol. Today 1992; 13: 219–224.

Wu H–Y, Russell MW. Induction Of Mucosal Immunity By Intranasal Application Of A Streptococcal Surface Protein Antigen With The Cholera Toxin B Subunit. Infection and Immunity 1993; 61:314–322.

Russell. MW, Wu H–Y. Distribution Persistence, And Recall Of Serum And Salvary Antibody Responses To Peroral Immunization With Protein Antigen I/II Of Streptococcus Mutants Coupled To The Cholera Toxin B Subunit. Infection and Immunity 1991; 59:4061–4070.

Elson CO, Ealding W. Generalized Systemic And Mucosal Immunity In Mice After Mucosal Stimulation With Cholera Toxin. J. Immunol. 1984; 132:2736–2741.

Elson CO. Cholera Toxin And Its Subunits As Potential Oral Adjuvants. Curr. Topics Microbiol. Immunol. 1989; 146:29–33.

Lycke N, Holmgren J. Strong Adjuvant Properties Of Cholera Toxin On Gut Mucosal Immune Responses To Orally Presented Antigens. Immunology 1986; 59:301–308.

Wilson AD, Stokes CR, Bourme FJ. Adjuvant Effect Of Cholera Toxin On The Mucosal Immune Response To Soluble Proteins. Differences Between Mouse Strains And Protein Antigens. Scand. J. Immunol. 1989; 29:739–745.

Wilson Ad, Clarke CJ, Stokes CR. Whole Cholera Toxin And B Subunit Act Synergistically As An Adjuvant For The Mucosal Immune Response Of Mice To Keyhole Limpet Haemocyanin. Scand. J. Immunol. 1990; 31:443–451.

Czerkinsky C, Russell MW, Lycke N, Lindblad M, Holmgren J. Oral Administration Of A Streptococcal Antigen Coupled To Cholera Toxin B. Subunit Evokes Strong Antibody Responses In Salivary Glands And Extramucosal Yissues. Infect. Immun. 1989; 57:1072–1077.

Holmgren J, Lycke N, Czerkinsky C. Cholera Toxin and Cholera B Subunit As Oral–Mucosal Adjuvant And Antigen Vector Systems. Vaccine 1993; 11:1179–1184.

Quiding M, Nordstrom I, Kilander A, Anderson G, Hanson LA, Holmgren J, Czerkinsky C. Intestinal Immune Responses In Humans. Oral Cholera Vaccination Induces Strong Intestinal Antibody Responses and Interferon –λ Production and Evokes Local immunological Memory. J. Clin Invest. 1991;88:143–148.

Svennerholm AM, Jertborn M, Gothefors L, Karim AMMM, Sack DA, Holmgren J. Mucosal Antitoxin and Antibacterial Immunity After Cholera Disease And After Immunization With A Combined B Subunit–Whole Cell Vaccine. J. Infect. Dis. 1984; 149:884–893.

Lycke N, Tsuji T, Holmgren J. The Adjuvant Effect Of Vibrio Cholerae And *E. Coli* Heat Labile Enterotoxins Is Linked To The Ability To Stimulate Camp. European Journal of Immunology 1992; 22:2277–2281.

Lycke N, Karlsson U, Sjölander A, Magnusson K–E. The Adjuvant Action Of Cholera Toxin Is Associated With An Increased Intestinal Permeability for Luminal Antigens. Scandinavian Journal of Immunology 1991; 33:691–698.

Gizurarson S, Tamura S, Kurata T, Hasiguchi K, Ogawa H. The Effect Of Cholera Toxin And Cholera Toxin B Subunit On The Nasal Mucosa Membrane. Vaccine 1991; 9:825–832.

Bromander A, Holmgren J, Lycke N. Cholera Toxin Stimulates Il–1 Production And Enhances Antigen Presentation By Macrophages in vitro. Journal of Immunology 1991; 146:2908–2914.

Anastassiou ED, Yamada H, Francis ML, Mond JJ, Tsokos GC. Effects Of Cholera Toxin On Human B Cells. Cholera Toxin Induces B Cell Surface DR Expression While It Inhibits Anti–$\mu$ Antibody–Induced Cell Proliferation. J. Immunol. 1990; 145:2375–2380.

Munoz E, Zubiaga AM, Merrow M, Sauter NP, Huber BT. Cholera Toxin Discriminates Between T Helper 1 and 2 cells In T Cell Receptor–Mediated Activation: Role of Camp In T Cell Proliferation. J. Exp. Med. 1990; 172:95–103.

Lycke N, Strober W. Cholera Toxin Promotes B Cell Isotype Differentiation. J. Immunol. 1989; 142: 3781–3787.

Wilson AD, Bailey M, Williams NA, Stokes CR. The in vitro Production of Cytokines By Mucosal Lymphocytes Immunized By Oral Administration Of Keyhole Limpet Hemocyanin Using Cholera Toxin As An Adjuvant. European Journal of Immunology 1991; 21:2333–2339.

Francis ML, Ryan J, Jobling MG, Holmes RK, Moss J, Mond JJ. Cyclic AMP–Independent Effects Of Cholera Toxin On B Cell Activation. II. Binding of Ganglioside $G_{M1}$ Induces B Cell Activation. Journal of Immunology 1992; 148: 1999–2005.

Woogen SD, Ealding W. Elson CO. Inhibition of Murine Lymphocyte Proliferation By The B Subunit Of Cholera Toxin. Journal of Immunology 1987; 139:3764–3770.

Garrone P, Banchereau J. Agonistic And Antagonistic Effects Of Cholera Toxin On Human B Lymphocyte Proliferation. Molecular Immunology 1993; 30:627–635.

Haack BM, Emmrich F, Resch K. Cholera Toxin Inhibits T Cell Receptor Signaling By Covalent Modification Of The CD3–Subunit. Journal of Immunology 1993; 150:2599–2606.

Abraham E, Robinson A. Oral Immunization With Bacterial Polysaccharide and Adjuvant Enhances Antigen–Specific Pulmonary Secretory Antibody Response And Resistance To Pneumonia. Vaccine 1991; 9:757–764.

Szu SC, Li X, Schneerson R, Vickers JH, Bryla D, Robbins JB. Comparative Immunogenicities Of VI Polysaccharide–Protein Conjugates Composed Of Cholera Toxin Or Its B Subunit As A Carrier Bound To High–Or Lower–Molecular–Weight VI. Infect. Immun. 1989; 57:3823–3827.

Chen K–S, Strober W. Cholera Holotoxin And Its B Subunit Enhance Peyer's Patch B Cell Responses Induced By Orally Administered Influenza Virus: Disproportionate Cholera Toxin Enhancement Of The IgA B Cell Response. Eur. J. Immunol. 1990; 20:433–436.

Liang X, Lamm ME, Nedrud JG. Oral Administration Of Cholera Toxin–Sendal Virus Conjugate Potentiates Gut And Respiratory Immunity Against Sendal Virus. Journal of Immunology 1988; 141:1495–1501.

Brimblecombe FSW, Cruicshank R, Masters PL, Reid DD, Stewart GT. Family Studies Of Respiratory Infections. British Medical Journal 1958; 119–128.

Masters PL, Brumfitt W, Mendez RL, Likar M. Bacterial Flora Of The Uupper Respiratory Tract In Paddington Families, 1952–1954. Brit. Med. J. 1958; 1:1200–1205.

Gwaitney JM, Sande MA, Austrian R, al. e. Spread Of *Streptococcus Pneumoniae* In Families: II Relation Of Transfer Of *Streptococcus Pneumoniae* To Incidence Of Colds And Serum Antibody. J. Infect Dis. 1975; 132–62.

Russell MW, Prince SJ, Ligthart GJ, Mestecky J, Radi J. Comparison Of Salivary And Serum Antibodies To Common Environmental Antigens In Elderly, Edentulous, And Normal Adult Subjects. Aging Immunol. Infect. Dis. 1990; 2:275–286.

Bessen D, Fischetti VA, Influence of Intranasal Immunization With Synthetic Peptides Corresponding To Conserved Epitopes Of M Protein On Mucosal Immunization By Group A Streptococci. Infect. Immun. 1988; 56: 2666–2672.

Hollingshead SK, Simecka JW, Michalek SM. Role Of M Protein In Pharyngeal Colonization By Group A Streptococci In Rats. Infect. Immun. 1993; 61:2277–2283.

Kauppi M, Eskola J, Kathty H.H. Influenzae Type B (Hib) Conjugate Vaccines Induce Mucosal IgA1 to IgA2 Antibody Responses In Infants And Children. ICAAC Abstracts 1993; 33:174.

Briles DE, Forman C, Horowitz JC, Volanakis JE, Benjamin WH Jr., McDaniel LS, Eldridge J, Brooks J. Antipneumococcal Effects of C–reactive Protein And Monoclonal Antibodies To Pneumococcal Cell Wall And Capsular Antigens. Infect. Immun. 1989; 57: 1457–1464.

Briles DE, Claftin JL, Schroer K, Forman C. Mouse IgG3 Antibodies Are Highly Protective Against Infection With *Streptococcus Pneumoniae*. Nature 1981; 294:88–90.

Lock RA, Paton JC, Hansman D. Comparative Efficacy of Pneumococcal Neuraminidase and Pneumolysin as Immunogens Protective Against *Streptococcus Pneumoniae*. Microb. Pathog. 1988; 5:461–467.

Lock RA, Hansman D, Paton JC. Comparative Efficacy Of Autolysin And Pneumolysin As Immunogens Protecting Mice Against Infection By *Streptococcus Pneumoniae*. Microbial Pathogenesis 1992; 12:137–143.

Converse GM III, Dillon HC Jr. Epidemiological Studies Of *Streptococcus Pneumoniae* In Infants: Methods of Isolating Pneumococci, J. Clin. Micro. 1977; 5:293–296.

Fontanges et al Rev. Fr. Allerogol 17:35–41, 1977 Abstract only.

Garcia et al FEMS Microbiol Lett 108:163–167 1993.

Kurl et al. Acta Path Microb. Immunol. 93:401–405 1985.

Germie et al Novel Vaccine Strategies, Mucosal Immunization, Adjuvants & Genetic Approaches Abstract 1993.

Bessen et al Journ of Immunology 145:1251–1256 1990.

Wu et al Infection & Immunity 61:314–322 1993.

van de Wijgert et al, Infection & Immunity 59 2750–2757, 1991.

Bixler et al Synthetic Vaccines vol. 1 Chapter 4 pp. 39–71, 1987.

Kurono et al, Abstracts of the 14th Midwinter Res Meeting Association for Res in Otolaryngology p. 56 Abst 178, 1991.

Yoshimura, Abstracts of the 5th Internation Symposium Recent Advances in Otitis Medic, p. 74 Abst 18, 1991.

Yother et al Journal of Bacteriology 174:610 618.

DOMAINS OF THE MATURE PspA

| | | | | | | a | b | c | d | e | f | g | |
|---|---|---|---|---|---|---|---|---|---|---|---|---|---|---|
| GLU | GLU | ser | pro | val | ala | ser | gln | ser | LYS | ala | GLU | LYS | ASP | 14 |
| | | | | | | | tyr | ASP | ala | ala | LYS | LYS | ASP | 21 |
| | | | | | | | ala | LYS | asn | ala | LYS | LYS | ala | 28 |
| | | | | | | | val | GLU | ASP | ala | gln | LYS | ala | 35 |
| | | | | | | | leu | ASP | ASP | ala | LYS | ala | ala | 42 |
| | | | | | | | gln | LYS | LYS | | | | | 45 |

FIG.3a

```
pspa - sequence -> 1-phase Translation
DNA and derived amino acid 2086 b.p.   AAGCTTATGATA.....TCTTTAGGTACC  linear
  1                                              31
AAG CCT ATG ATA TAG AAA TTT AAT ATA CTT ATA AAG AAA AAA ATG TAA TAT AAA ACA CTT GAC AAA TAT TTA
                                                 91
 61
CGG AGG AGG CTT ATA CTT ATA AAT AAG AAA ATG ATT TTA TGA AAA TGA CTA TCA GAA AAG AGG TAA
                                                151
121
ATT TAG ATG AAT AGT GTT GTT CAG TCT AAA ATG ACA AGT CTA GCC AGC GTC GCT ATC TTA GGG
        met asn                  lys met thr ser leu ala ser val ala ile leu gly
                                                211
181
GCT GGT TTT GTT GCG GAG TCT AAA CCT ACT GTA GCA GAA CTA GCT GAA TCT GCC GTA GCC AGT
ala gly phe val ala glu ser lys pro thr val ala glu leu ala glu ser ala val ala ser
                                                271
241
CAG TCT AAA AAA GCT GAG GAC GAG TAT GAT GCG GCA AAA AAG GAT GCT GAT GCT AAG AAA AAA
gln ser lys lys ala glu asp glu tyr asp ala ala lys lys asp ala asp ala lys lys lys
                                                331
301
GCA GTA GAA CAG GCT AAG AAG CAA AAG CTA CTA TAT CAA GCT CTA CTA TAT CAG GCT ATG GAC
ala val glu gln ala lys lys gln lys leu leu tyr gln ala leu leu tyr gln ala met asp
                                                391
361
GAG CAG GCA AAA GTG GCA GCA GAT ATG AAG GAA TAT TAT AAG TAT GAG CAC ACA GAG TTG AAA
glu gln ala lys val ala ala asp met lys glu tyr tyr lys tyr glu his thr glu leu lys
                                                451
421
GAT AAA GCA ACT ACT TTT GCC AAG AGA CGA GCT CCT CCT GAA GTT GAG GAT ATG ACG TTT CTA
asp lys ala thr thr phe ala lys arg arg ala pro pro glu val glu asp met thr phe leu
                                                511
481
GCC GCA GCA GTA GCA GCA GCA GCT GAA GCA GGT CGT ACA AAA GAA GCA GAG GAG GTT CAT CGA
ala ala ala val ala ala ala ala glu ala gly arg thr lys glu ala glu glu val his arg
                                                571
541
AAA ACT AAT AAA ATC CGA AAA CAA AAA GCT CCA GCA CCA CCT GAA GAA AAA AAA GCA AAA CAA
lys thr asn lys ile arg lys gln lys ala pro ala pro pro glu glu lys lys ala lys gln
                                                631
601
ACT AAA AAA TCA GAA GAA GCT GAT GCT CTT GTA CTA GAA CTT GAG CTT GAA ACT CTA
thr lys lys ser glu glu ala asp ala leu val leu glu leu glu leu glu thr leu
```

FIG. 3b

| Pos | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 661 | GAA glu | GCT ala | AAA lys | GCA ala | AAA lys | TTA leu | AAA lys | GAA glu | GAG glu | AAA lys | AAA lys (691) | GCC ala | GAA glu | AAA lys | CAA gln | AAA lys | GTG val | | | |
| 721 | GAT asp | GCT ala | GAA glu | AAA lys | GAA glu | GAG glu | GCT ala | CCT pro | AAA lys | GAA glu | ATC ile (751) | AAT asn | ACT thr | CAA gln | CAT his | AAA lys | AGA arg | | | |
| 781 | CTA leu | GAA glu | CAA gln | GCT ala | GTC val | CTC leu | GCT ala | CAA gln | AAA lys | ATT ile | TCT ser (811) | TAT tyr | TTG leu | GCT ala | GAA glu | GAA glu | GGT gly | | | |
| 841 | TTC phe | CCT pro | GAT asp | CTT leu | CTT leu | AAA lys | AAA lys | ATT ile | TCA ser | GAG glu | TCA ser (871) | GAA glu | CTA leu | CAT asp | TCA ser | CTT leu | GAA glu | | | |
| 901 | CAG gln | AGT ser | GCT ala | AAA lys | CCT pro | CAA gln | AAA lys | ATT ile | AAA lys | TCA ser | GCG ala (931) | AAA lys | ATT ile | GAT asp | AAA lys | CAA gln | CTT leu | | | |
| 961 | TTA leu | GCT ala | CAA gln | GAT asp | AAG lys | GCC ala | AAT asn | TTA leu | ATT ile | TTT phe | GCT ala (991) | TAC tyr | TTG leu | GAA glu | AAA lys | AAA lys | ACT thr | | | |
| 1021 | AAA lys | GCT ala | AAA lys | GAA glu | AAA lys | GAT asp | GTA val | AAA lys | AAA lys | GCA ala | GAC asp (1051) | CTT leu | GAA glu | CAA gln | GCA ala | GAG glu | AAT asn | | | |
| 1081 | ATT ile | GCT ala | CCA pro | GCG ala | AAA lys | GAA glu | CCA pro | GCT ala | AAA lys | AAT asn | ACT thr (1111) | CCA pro | AAA lys | CCA pro | TTA leu | GCA ala | CAA gln | | | |
| 1141 | GAG glu | CCT pro | GAT asp | TAT tyr | CCA pro | AAA lys | GCT ala | CCT pro | GAT asp | ACT thr | ACT thr (1171) | CCT pro | GAC asp | TAT tyr | GAG glu | CGT arg | GAA glu | | | |
| 1201 | CCA pro | AAA lys | GCG ala | CCA pro | CAA gln | CAA gln | GCT ala | GCT ala | AAA lys | CCT pro | ACT thr (1231) | ACT thr | CCA pro | AAA lys | GCT ala | CCA pro | CCT pro | | | |
| 1261 | CAA gln | CCA pro | TAT tyr | ACA thr | CAA gln | TTG leu | ACA thr | CAA gln | CAG gln | AAT asn | CCC pro (1291) | CCA pro | GAC asp | CAA gln | AAA lys | AAA lys | ACT thr | | | |
| 1261 | GAA glu | GAA glu | AAT asn | GGC gly | TTG leu | AAA lys | AAA lys | GAG glu | CAA gln | AAC asn | CAA gln (1351) | CAA gln | CTT leu | TTC phe | TAC tyr | AAT asn | GGT gly | | | |
| 1321 | GCA ala | CCA pro | CCA pro | ACA thr | CCA pro | TGG trp | ATG met | ATG met | GGT gly | AAC asn | | | | | | | | | | |

FIG.3c

| | | | | | | | | | | | | | | | |
|---|---|---|---|---|---|---|---|---|---|---|---|---|---|---|---|
| 1381 TCA ser | ATG met | GCG ala | ACA thr | GGA gly | TGG trp | CTC leu | CAA gln | AAC asn | AAC asn | 1411 GGT gly | TCA ser | TGG trp | TAC tyr | TAC tyr | CTC leu | AAC· asn | AGC ser | AAT asn | GGT gly |
| 1441 GCT ala | ATG met | GCT ala | ACA thr | GGT gly | TGG trp | CTC leu | CAA gln | AAC asn | AAT asn | GGT gly 1471 | TCA ser | TGG trp | TAT tyr | TAC tyr | CTC leu | AAC asn | GCT ala | AAC asn | GGC gly |
| 1501 GCT ala | ATG met | GCA ala | ACA thr | GGT gly | TGG trp | CTC leu | TAC tyr | TAC tyr | AAC asn | GGT gly 1531 | TCA ser | TGG trp | TAC tyr | TAC tyr | CTC leu | AAC asn | GCT ala | AAT asn | GGT gly |
| 1561 GCT ala | ATG met | GCT ala | ACA thr | GGT gly | TGG trp | CTC leu | CAA gln | GTC val | AAC asn | GGT gly 1591 | TCA ser | TGG trp | TAT tyr | TAC tyr | CTC leu | AAC asn | GCT ala | AAC asn | GGC gly |
| 1621 GCT ala | ATG met | GCA ala | ACA thr | GGT gly | TGG trp | GCT ala | CAA gln | TAC tyr | AAT asn | GGT gly 1651 | TCA ser | TGG trp | TAC tyr | TAC tyr | CTC leu | AAC asn | GCT ala | AAT asn | GGT gly |
| 1681 GCT ala | ATG met | GCT ala | ACA thr | GGT gly | TGG trp | CTC leu | AAA lys | GTC val | AAC asn | GGT gly 1711 | TCA ser | TGG trp | TAC tyr | TAC tyr | CTC leu | AAC asn | GCT ala | AAC asn | GGT gly |
| 1741 GCT ala | ATG met | GCA ala | ACA thr | GGT gly | TGG trp | GCT ala | CAA gln | TAC tyr | AAC asn | GGT gly 1771 | TCA ser | TGG trp | TAC tyr | TAC tyr | CTC leu | AAC asn | GCT ala | AAT asn | GGC gly |
| 1801 GCT ala | ATG met | GCT ala | ACA thr | GGT gly | TGG trp | GTG val | AAA lys | GTC val | AAC asn | GGT gly 1831 | ACC ser | TGG trp | TAC tyr | TAC tyr | CTT leu | AAC asn | GCT ala | AAT asn | GGT gly |
| 1861 GCT ala | ATG met | GCA ala | GCA ala | AGC ser | CAA gln | TGG trp | TTC phe | GAT asp | GGA gly | GAT asp 1891 | GAT asp | AAA lys | TGG trp | TAT tyr | TAT tyr | GAA glu | GCT ala | TCA ser | GGC gly |
| 1921 GCT ala | ATG met | AAA lys | GCA ala | GTC val | AAC asn | ACA thr | ACT thr | GTA val | GTA val | TCA ser 1951 | TAT tyr | AAA lys | AAA lys | TGG trp | GTC val | CTT leu | GCC ala | AAT asn | GGT gly |
| 1981 GCC ala | GCC ala | CTT leu | GCA ala | GTC val | ATT ile | AAC asn | TTC phe | GCA ala | TAA OCH | GGC gly 2011 | CAT his | AAA lys | AAA lys | TTG leu | ACA thr | TAT tyr | GCC ala | TGA OPA | TTA leu |
| 2041 GTT val | TAA OCH | TAA OCH | GAT asp | AGC ser | TTG leu | AAT asn | TTT phe | TGT cys | TAA OCH | GAA glu 2071 | TTC phe | TTT phe | AAA lys | TTT phe | ATG met | TTT phe | AAT asn | GGT gly | TGG trp |
| AAG lys | CTT val | AGA arg | TTG leu | AAT asn | AGA arg | TTT phe | AGA arg | AGG tyr | TAC tyr | GTA val | TTC phe | | | | | TAA OCH | | GAA glu | AAA lys |

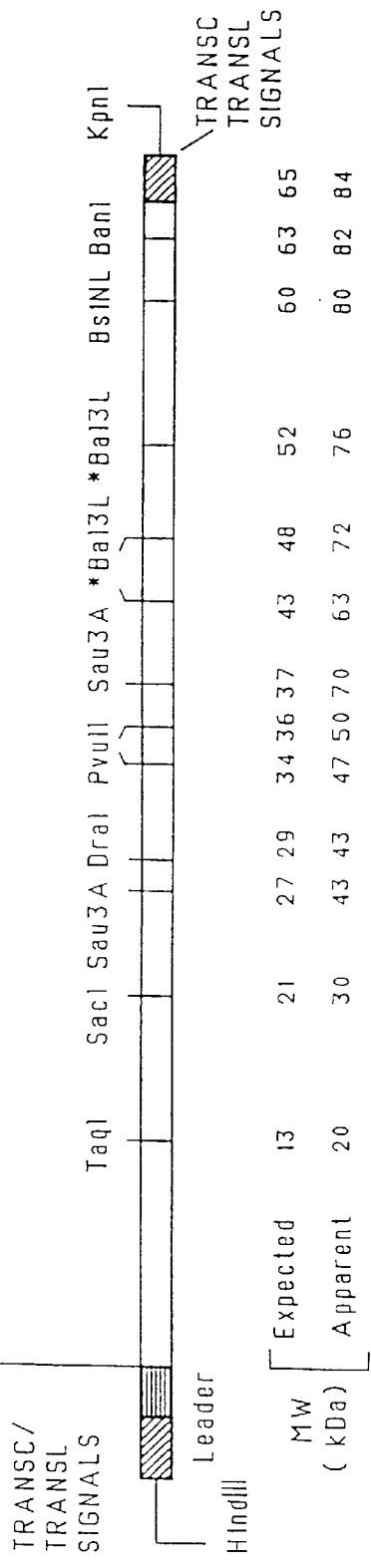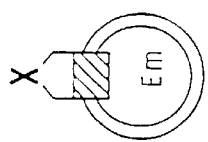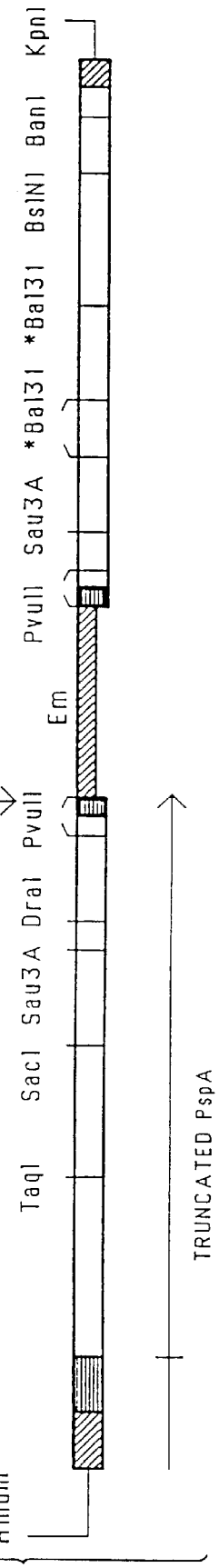
FIG.4A
FIG.4B

Location of epitopes detected by monoclonal antibodies to PspA

|  |  | a | b | c | d | e | f | g |
|---|---|---|---|---|---|---|---|---|
|  | 1 | E | E | s | p | y | a | s |
|  | 8 | Q | s |   |   |   |   |   |
|  | 15 | y | D | K | a | a | E | K |
|  | 15 | y | D | a | a | K | K | D |
|  | 22 | a | K | N | a | K | K | a |
|  | 29 | v | E | D | a | Q | K | a |
|  | 36 | L | D | D | a | K | a | a |
| XI1526* | 43 | Q | K | K | y | D | E | D |
| XI126* | 50 | Q | K | K | t | E | E | K |
| XIR35 | 57 | a | a | l | E | K | a | a |
| XIR148 | 64 | s | E | E | m | D | K | a |
| XIR1224 | 71 | v | a | a | v | Q | Q | a |
|  | 78 | y | L | a | y | Q | Q | a |
|  | 85 | t | D | K | a | a | K | D |
|  | 92 | a |   |   |   |   |   |   |
|  | 97 | L | D | E | a | a | D | K | m |
|  | 97 | L | D | E | a | K | K | R |
|  | 104 | E | E | E | a | K | t | K |
|  | 111 | L | N | t | v | R | a | m |
|  | 118 | v | v | p | E | p | E | Q |
|  | 125 | L | a | E | t | K | K | K |
| 138 HHHHH | 132 | s | E | E | a | K | Q | K |
|  | 139 | a | p | E | L | t | K | K |
|  | 146 | L | E | E | a | K | a | K |
|  | 153 | L | E | E | a | E | K | K |
|  | 160 | a | t | E | a | K | Q | K |
| XIR16 | 167 | v | D |   |   |   |   |   |
|  | 174 | p | Q | a | a | E | E | v | a |
|  | 178 | i | a | E | L | E | N | K |
|  | 178 | i | a | E | L | E | N | Q |
|  | 185 | v | H | R | L | E | Q | E |
| 193 HHHHH | 192 | L | K | E | i | D | E | s |
|  | 199 | E |   |   |   |   |   |   |
|  | 204 | a | K | E | g | s | E | D | y |
|  | 204 | a | K | E | g | L | R | a |
|  | 211 | p | L | Q | s | K | L | D |
| X164* | 218 | a | K | K | a | K | L | s |
| XIR278* | 225 | K |   |   |   |   |   |   |
| XI1325* | 226 | L | E | E | L | s | D | K |
|  | 233 | L | D | E | L | D | a | E |
|  | 240 | i | a | K | L | E | D | Q |
|  | 247 | L | K | a | a | E | E | N |
|  | 254 |   | N | N | v | E | D | y |
| 261 HHHHH | 260 | L | K | E | g | L | E | K |
|  | 267 | t | L | a | a | K | K | a |
| XI1323* | 274 | E |   |   |   |   |   |   |
|  | 275 | L | E | K | t | E | a | D |
|  | 282 | L | K | K | a | v | N | E |

FIG.5

ANTIBODY REACTIVITY

| | Xi 126 | XiR 1224 | XiR 148 | XiR 1526 | XiR 35 | XiR 16 | XiR 278 | XiR 1325 | XiR 64 | XiR 1323 |
|---|---|---|---|---|---|---|---|---|---|---|
| KSD 1014 | ++ | ++ | ++ | ++ | ++ | ++ | ++ | ++ | ++ | ++ |
| JY 4306 | ++ | ++ | ++ | ++ | ++ | ++ | + | ++ | ++ | ++ |
| JY 4310 | ++ | + | ++ | ++ | ++ | ++ | – | – | – | – |
| JY 4285 | ++ | + | ++ | ++ | ++ | + | – | – | – | – |
| KSD 1500 | – | – | – | – | – | – | – | – | – | – |
| BC 100 | – | – | – | – | – | – | ++ | ++ | ++ | ++ |
| BC 207 | – | – | – | – | – | + | ++ | ++ | ++ | ++ |

FIG. 6

IMMUNOGENIC COMPOSITIONS FOR MUCOSAL ADMINISTRATION OF PNEUMOCOCCAL SURFACE PROTEIN A (PSPA)

REFERENCE TO RELATED APPLICATIONS

This application is a continuation-in-part of U.S. patent application Ser. No. 08/312,949, filed Sep. 30, 1994, which itself is a continuation-in-part of U.S. patent application Ser. No. 08/246,636 filed May 20, 1994, which itself is a continuation-in-part of U.S. patent application Ser. No. 08/048,896 filed Apr. 20, 1993, (now abandoned) which itself is a continuation-in-part of U.S. patent application Ser. No. 07/835,698 filed Feb. 12, 1992, (now abandoned), which itself is a continuation-in-part of U.S. patent application Ser. No. 07/656,773 filed Feb. 15, 1991 (now abandoned). The disclosure of such related applications are incorporated herein by reference.

FIELD OF THE INVENTION

This invention relates to mucosal immunization or administration of hosts, animals or humans, with pneumococcal antigens to stimulate an immunological response and preferably provide protection against pneumococcal colonization and systemic infection, and compositions therefor.

BACKGROUND

*Streptococcus pneumoniae* causes more fatal infections world-wide than almost any other pathogen (refs. 1, 2,—a list of the references appears at the end of the disclosure; and each reference is hereby incorporated herein by reference). In the U.S.A., deaths caused by *S. pneumoniae* rival in numbers those caused by AIDS (ref. 1). In the U.S.A., most fatal pneumococcal infections occur in individuals over 65 years of age, in whom *S. pneumoniae* is the most common cause of community-acquired pneumonia. In the developed world, most pneumococcal deaths occur in the elderly, or in immunodeficient patents including those with sickle cell disease. In the less-developed areas of the world, pneumococcal infection is one of the largest causes of death among children less than 5 of age (refs. 3, 4, 5, 6). The increase in the frequency of multiple antibiotic resistance among pneumococci and the prohibitive cost of drug treatment in poor countries make the present prospects for control of pneumococcal disease problematical (refs. 7, 8, 9).

The reservoir of pneumococci that infect man is maintained primarily via nasopharyngeal human carriage. Humans acquire pneumococci through aerosols or by direct contact. Pneumococci first colonize the upper airways and can remain in nasal mucosa for weeks or months. As many as 50% or more of young children and the elderly are colonized. In most cases, this colonization results in no apparent infection (refs. 10, 11, 12). Studies of outbreak strains have suggested that even highly virulent strains can colonize without causing disease (refs. 13, 14, 15, 16). These expectations have been recently confirmed using molecular probes to fingerprint individual clones (M. J. Crain, personal communication to one of the inventors). In some individuals, however, the organism carried in the nasopharynx can give rise to symptomatic sinusitis or middle ear infections. If pneumococci are aspirated into the lung, especially with food particles or mucus, they can cause pneumonia. Infections at these sites generally shed some pneumococci into the blood where they can lead to sepsis, especially if they continue to be shed in large numbers from the original focus of infection. Pneumococci in the blood can reach the brain where they can cause meningitis. Although pneumococcal meningitis is less common than other infections caused by these bacteria, it is particularly devastating; some 10% of patients die and greater than 50% of the remainder have life-long neurological sequelae (refs. 17, 18).

In elderly adults, the present 23-valent capsular polysaccharide vaccine is about 60% effective against invasive pneumococcal disease with strains of the capsular types included in the vaccine (refs. 19, 20). The 23-valent vaccine is not effective in children less than 2 years of age because of their inability to make adequate responses to most polysaccharides (refs. 21, 22). Improved vaccines that can protect children and adults against invasive infections with pneumococci would help reduce some of the most deleterious aspects of this disease. A vaccine that protected against disease but did not reduce pneumococcal carriage rates would not, however, be expected to control the disease in immuno-compromised (ref. 20) and in unimmunized individuals. Such a vaccine would also not be expected to affect the rates of infection in immunized children prior to the development of an adequate anti-vaccine response.

A strategy that could control infections in all of these individuals would be any form of immunization that prevented or greatly reduced carriage, and hence transmission of pneumococci. In the case of immunization of young children with *Haemophilus influenzae* group b polysaccharide-protein conjugates, it has been observed that carriage is reduced from about 4% to less than 1%, (ref. 23), a possible explanation of concomitant herd immunity (ref. 24). If a vaccine could prevent colonization by pneumococci, such vaccine would be expected to prevent virtually all pneumococcal infections in the immunized patients. Since even unimmunized patients must acquire pneumococci from others, a vaccine that reduced carriage should reduce infections in immuno-compromised as well as unimmunized patients. In fact, an aggressive immunization program, coupled with antibiotic treatment of demonstrated carriers, might be able to largely eliminate the human reservoir of this organism. It may not be possible, however, to totally eliminate pneumococci since there are a number of reports that they have been found in laboratory rodents (ref. 25). Whether these pneumococci are infectious for man, easily transmittable to man, or even pathogens in wild rodents is not known. *S. pneumoniae* does not live free in the environment.

Although intramuscular immunization with capsular polysaccharide vaccines has been effective at reducing the incidence of pneumococcal sepsis in the elderly (ref. 20), it has not been reported to affect pneumococcal carriage rates in children up to 54 months of age (refs 26, 27). Whether the conjugate vaccine will reduce carriage in children is not known. Thus, the search for a vaccine which can reduce rates of nasopharyngeal carriage must include an examination of non-capsular antigens. Since immunity to carriage would be expected to operate at the mucosal surface, any attempt to identify antigens for vaccines against carriage should include immunizations designed to elicit mucosal immune responses. Accordingly, the intranasal immunization or administration with pneumococcal proteins, as in the present invention has not, it is believed been heretofore disclosed or suggested or, in addition, the evaluation of polysaccharide-protein conjugates, as in the present disclosure, has not it is believed been heretofore taught or suggested.

SUMMARY OF THE INVENTION

In accordance with the present invention, it has now been surprisingly found that mucosal administration, preferably intranasally, of pneumococcal surface protein A (PspA) or an immunogenic fragment thereof elicits an immunological response and can even provide protection to a host against pneumococcal colonization and/or systemic infection.

Accordingly, in one aspect, the present invention provides a method of protecting a host, preferably a human host, against colonization by pneumococci and/or systemic infection by mucosal administration, preferably by intranasal administration, to the host of an effective amount of at least one pneumococcal surface protein A (PspA) and/or an immunogenic fragment thereof containing at least one protection-eliciting epitope.

In another aspect, the present invention provides a method of eliciting an immunological response in a host against pneumococci and/or systemic infection by mucosal-administration, preferably intranasal administration, to the host of an effective amount of at least one PspA and/or an immunogenic fragment thereof containing at least one epitope. More preferably, the response is protective and the epitope is protection-eliciting.

The PspA may be in the form of killed whole *S. pneumoniae* or a lysate of whole *S. pneumoniae*. Alternatively, the PspA may be in the form of purified isolated protein or a fragment thereof. Such purified and isolated protein or fragment thereof (individually and/or collectively, for purposes only of shorthand in this specification, "PspA") may be obtained from bacterial isolates or may be formed recombinantly. The PspA is preferably in a vaccine or immunogenic composition. Such a composition can include a pharmaceutically acceptable adjuvant and/or a pharmaceutically acceptable carrier.

Immunogenic compositions including vaccines may be prepared as inhalables, sprays and the like (e.g., nasal spray, aerosol spray or pump spray and the like), e.g., as liquid solutions or emulsions, etc. Aerosol spray preparations can be in a pressurized container with a suitable propellant such as a hydrocarbon propellant. Pump spray dispensers can dispense a metered dose or, a dose having a particular particle or droplet size. Pump spray dispensers are commercially available, e.g., from Valois of America, Inc., Connecticut. Nasal spray dispensers are commonly fabricated from a flexible material such as plastic and cause a spray to dispense in response to being squeezed. Anti-inflammatories, such as "Vanceril" are commercially available in oral and nasal aerosol form for mucosal administration; the anti-inflammatory "Vancerase" is commercially available in a pump-spray dispenser for nasal administration; cold remedies such as "Dristan" are commercially available in nasal spray (squeeze) dispensers (so that the reader is aware that aerosol, pump and squeeze dispensers are known and available).

The PspA may be mixed with pharmaceutically acceptable excipients which are compatible with the PspA. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

Immunogenicity can be significantly improved if the antigen (PspA) is co-administered with an adjuvant, commonly used as 0.05 to 0.1 percent solution in phosphate buffered saline. Adjuvants enhance the immunogenicity of an antigen (PspA) but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune responses (HIR) and cell-mediated immunity (CMI), immunogens are preferably emulsified in adjuvants.

Desirable characteristics of ideal adjuvants include any or all of:

(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al. on Aug. 8, 1989 which is incorporated herein by reference thereto teaches glycolipid analogs including N-glycosylamides, N-glycosylureas and Nglycosylcarbamates, each of which is substituted in the sugar residue by an amino acid, as immune-modulators or adjuvants. Thus, Lockhoff et al. (U.S. Pat. No. 4,855,283) reported that N-glycolipid analogs displaying structural similarities to the naturally occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugars through the anomeric carbon atom, to mimic the functions of the naturally occurring lipid residues.

U.S. Pat. No. 4,258,029 granted to Moloney, assigned to Connaught Laboratories Limited and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Octodecyl esters of aromatic amino acids complexed with a recombinant hepatitis B surface antigen, enhanced the host immune responses against hepatitis B virus.

In a preferred aspect of the invention, the PspA is administered with cholera toxin B as an adjuvant.

The mucosal administration preferably is effected intranasally, e.g., to the olfactory mucosa, to provide protection to the host against both pneumococcal colonization and systemic infection. The intranasal administration also may provide protection to the host against pulmonary infection as well as protection to the host against an infection starting as a pulmonary infection. However, the mucosal administration can also involve respiratory mucosa, gingival mucosa or alveolar mucosa. Thus, the administration can be perlingual or sublingual or into the mouth or respiratory tract; but intranasal administration is preferred.

Compositions of the invention, especially for nasal administration, are conveniently provided as isotonic aqueous solutions, suspensions or viscous compositions which may be buffered to a selected pH. The viscous compositions may be in the form of gels, lotions, ointments, creams and the like and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer.

Liquid sprays and drops are normally easier to prepare than gels and other viscous compositions. Additionally, they are somewhat more convenient to administer, especially in multi-dose situations. Viscous compositions, on the other hand can be formulated within the appropriate viscosity range to provide longer contact periods with mucosa, such as the nasal mucosa.

Suitable nontoxic pharmaceutically acceptable carriers, and especially nasal carriers, will be apparent to those skilled in the art of pharmaceutical and especially nasal pharmaceutical formulations. For those not skilled in the art, reference is made to the text entitled "REMINGTON'S PHARMACEUTICAL SCIENCE", 17th edition, 1985, incorporated herein by reference. Obviously, the choice of suitable carriers will depend on the exact nature of the particular mucosal dosage form, e.g., nasal dosage form, required [e.g., whether the composition is to be formulated into a solution such as a nasal solution (for use as drops or as a spray), a nasal suspension, a nasal ointment, a nasal gel or another nasal form]. Preferred mucosal and especially nasal dosage forms are solutions, suspensions and gels, which normally contain a major amount of water (preferably purified water) in addition to the antigen (PspA). Minor amounts of other ingredients such as pH adjusters (e.g., a base such as NaOH), emulsifiers or dispersing agents, buffering agents, preservatives, wetting agents and jelling agents (e.g., methylcellulose) may also be present. The mucosal (especially nasal) compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Compositions within the scope of this invention can contain a humectant to inhibit drying of the mucous membrane and to prevent irritation. Any of a variety of pharmaceutically acceptable humectants can be employed including, for example sorbitol, propylene glycol or glycerol. As with the thickeners, the concentration will vary with the selected agent, although the presence or absence of these agents, or their concentration, is not an essential feature of the invention.

Enhanced absorption across the mucosal and especially nasal membrane can be accomplished employing a pharmaceutically acceptable surfactant. Typically useful surfactants for compositions include polyoxyethylene derivatives of fatty acid partial esters of sorbitol anhydrides such as Tween 80, Polyoxyl 40 Stearate, Polyoxyethylene 50 Stearate and Octoxynol. The usual concentration is form 1% to 10% based on the total weight.

A pharmaceutically acceptable preservative can be employed to increase the shelf-life of the compositions. Benzyl alcohol may be suitable, although a variety of preservatives including, for example, Parabens, thimerosal, chlorobutanol, or bezalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to PspA. This will present no problem to those skilled in chemical and pharmaceutical principles, or problems can be readily avoided by reference to standard texts or by simple experiments (not involving undue experimentation), from this disclosure.

The therapeutically effective compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical arts taking into consideration such factors as the age, sex, weight, and condition of the particular patient, and the mucosal route of administration. Dosages for humans or other mammals can be determined without undue experimentation by the skilled artisan, from the Examples below (e.g., from the Examples involving mice).

In particular aspect of the invention, there is provided a method of immunization of a host against colonization with *Streptococcus pneumoniae* in the nasopharynx, which comprises intranasally administering to the host an immunizing amount of pneumococcal surface protein A (PspA) in the form of a killed whole pneumococci, a lysate of pneumococci or an isolated PspA or an immunogenic fragment thereof.

The present invention further provides a vaccine composition or immunogenic composition for mucosal, preferably intranasal, administration to a host to confer protection or elicit an immunological response, against colonization with *S. pneumoniae*, preferably in the nasopharynx, which comprises:

a vaccine or immunogenic composition for mucosal, preferably intranasal administration to a host to confer protection against colonization with S. pneumoniae in preferably the nasopharynx, which comprises:

an effective amount of a pneumococcal surface protein A (PspA) in the form of a killed whole pneumococci, a pneumococcal lysate, an isolated and purified PspA or an immunogenic fragment thereof containing at least one epitope, preferably protection-eliciting epitope, an adjuvanting amount of an adjuvant, preferably the B subunit of cholera toxin, and optionally a pharmaceutical carrier therefor.

WO 92/14488 is incorporated herein by reference.

In published International patent application WO 92/14488, there are described the DNA sequences for the pspA gene from S. pneumoniae Rx1, the production of a truncated form of PspA by genetic engineering and the demonstration that such truncated form of PspA confers protection in mice to challenge with live pneumococci.

From sequences of the pspA gene, it has been shown that PspA proteins are variable in size (roughly 70 kDa). The C-terminal 37% of the molecule is largely composed of the 20-amino acid repeats which form a binding site that permits PspA to attach to the phosphocholine residues of the pneumococcal lipoteichoic acids. The central region of PspA is rich in prolines and is suspected to be the portion of the molecule that passes through the cell wall. The sequence of the N-terminal 80% of the molecule is largely α-helical and contains the region of PspA that can elicit antibodies that are protective against sepsis. Although PspA's are almost always at least slightly different from one another, there is enough cross-reactivity between them that antibodies to one PspA detect PspAs on all pneumococci. Moreover, immunization with one PspA can either protect against death or delay death with virtually all different challenge strains. Accordingly, a mixture of a small number of PspAs could elicit effective immunity against most pneumococci.

The immunoprotective truncated PspAs described in WO 92/14488 may be used in the present invention as the PspA fragments described above for mucosal administration.

The ability of a vaccine to protect against pneumococcal colonization, as provided herein, means that the active component may protect against disease not only in the immunized host but, by eliminating carriage among immunized individuals, the pathogen and hence any disease it causes may be eliminated from the population as a whole.

In the data presented herein, it is shown that intranasal administration can also prevent sepsis resulting from intratracheal administration of pneumococci, so that the vaccine can protect against both pneumococcal colonization and sepsis (systemic infection).

GENERAL DESCRIPTION OF INVENTION

The principal determinant of specific immunity at mucosal surfaces is secretory IgA (S-IgA) which is physiologically and functionally separate from the components of the circulatory immune system. S-IgA antibody responses may be induced locally by the application of suitable immunogens to a particular mucosal site. The bulk of mucosal S-IgA responses, however, are the results of immunity generated via the common mucosal immune system (CMIS) (ref. 28), in which immunogens are taken up by specialized lympho-epithelial structures, collectively referred to as mucosa-associated lymphoid tissue (MALT). The best studied immunologic lympho-epithelial structures are the gut-associated lymphoid tissues (GALT), such as intestinal Peyer's patches. It is now clear, however, that other structurally and functionally similar lymphoid follicles occur at other mucosal surfaces, including those of the respiratory tract (ref. 29).

Bronchus-associated lymphoid tissue (BALT) was described by Bienenstock (refs. 30, 31) in experimental animals, but is apparently not present in the noninfected human bronchial tree (ref. 32). The upper respiratory tract in humans, however, is furnished with Waldeyer's ring of tonsils and adenoids. In rodents, the functional equivalent of these consists of nasal-associated lymphoid tissue (NALT), a bilateral strip of lymphoid tissue with overlying M-like epithelial cells at the base of the nasal passages (ref. 33).

In the experimental results set forth in the Examples below, it is shown that mice can be effectively immunized by intranasal (i.n.) instillation of bacterial protein immunogens, particularly when conjugated to or mixed with cholera toxin (CT) or its B subunit (CTB) (ref. 34). When CTB is used as an adjuvant for i.n. immunizations, specific IgA antibodies are induced in secretions of the intestinal, respiratory, and genital tracts, as well as predominantly IgA antibody-secreting cells in the intestinal lamina propria and salivary glands. Strong circulatory immune responses are also induced, with IgG and IgA antibodies in the serum, and IgG and IgA antibody-secreting cells in the spleen. The circulatory (or systemic) immune responses elicited by i.n. administration of antigens along with CTB are comparable with, or even stronger than, those induced by the administration of similar immunogens by the intragastric (i.g.; peroral) route (refs. 34, 35). Accordingly, it appears that i.n. immunization is an effective route for stimulating common mucosal responses as well as circulatory antibody responses and requires less antigen than i.g. immunization.

Most soluble or non-replicating antigens are poor mucosal immunogens, especially by the peroral route, probably because they are degraded by digestive enzymes and have little or no tropism for the GALT. A notable exception is CT, which is a potent mucosal immunogen (ref. 36), probably because of the $G_{MI}$ ganglioside-binding property of its binding subunit, CTB, that enables it to be taken up by the M cells of Peyer's patches and passed to the underlying immunocompetent cells. In addition to being a good mucosal immunogen, CT is a powerful adjuvant (refs. 37, 38, 39). When administered in μg doses, CT greatly enhances the mucosal immunogenicity of other soluble antigens co-administered with it.

In the experimental results contained in the Examples below, it is shown that CTB is a strong adjuvant when given i.n. in mice along with the pneumococcal protein, PspA. Although the inventors cannot completely rule out a role for small amounts of CT in these studies, CT was <0.1% of the 5 μg dose of CTB that was administered. Thus, it would appear that when administered i.n., CTB may be a stronger adjuvant and act more independently of CT, than when it is given i.g. For example, when given orally or i.g., CTB has no direct adjuvant effect, but can act synergistically with CT (ref. 40).

The mechanisms by which CT and CTB act as adjuvants are not fully understood, but are certainly complex, and appear to depend on several factors, including: 1) the toxic activity associated with the ADP-ribosylating property of the Al subunit (ref. 41); 2) increased permeability of mucosae (refs. 42, 43), 3) enhanced antigen-presenting cell function (with increased levels of IL-1) (refs. 44, 45), as well as 4) direct stimulation of T and B cell activities (refs. 46, 47, 48, 49). This last point is controversial, however, as the in vitro effects of CT or CTB on T and B cells are generally inhibitory rather than stimulatory (refs. 50, 51, 52). Nevertheless, numerous reports attest to the in vivo mucosal immunoenhancing effects of CT and of CTB coupled to antigens (refs. 38, 39, 53, 54, 55, 56).

Although carriage of pneumococci can be maintained for long periods in the very young and the elderly, it is generally not a permanent condition. Carriage is much less common in older children and young adults (refs. 10, 11, 12, 57, 58). One explanation for these findings is that carriage may be interfered with by immunity (possibly mucosal immunity) to pneumococci (refs. 11, 59). The inventors have shown that most human saliva have IgA antibodies to type 23 capsular polysaccharide and phosphocholine (an immunodominant determinant of pneumococcal cell wall teichoic acids (ref. 60)). It seems likely, therefore, that human sera would also contain antibodies to other pneumococcal antigens. In the case of group A streptococci, M proteins have been shown to be required for colonization in rats, and antibodies to M proteins can protect against colonization of the throat (refs. 61, 62). In mice, the inventors have shown herein that antibody to PspA can prevent carriage of S. pneumoniae.

Antibodies may be effective against carriage in two ways, namely: 1) they might act at the mucosal surface by opsonizing pneumococci, preventing attachment or surface invasion; 2) they might act via opsonophagocytosis and killing. This latter mechanism could be especially important if nasopharyngeal carriage is dependent on minimal invasion of the nasal mucosal surface. The complement fixing antibodies could prevent the invasion and facilitate the killing of any pneumococci that invaded locally. Alternatively, complement fixing antibodies might be able to act and the mucosal surface if inflammation causes a sufficient release of complement, phagocytes, and possibly serum antibody.

One of these mechanisms might play a role in the observation that carriage of H. influenzae can be prevented by an intramuscular vaccine (ref. 23). It has recently been reported that significant levels of H. influenzae polysaccharide-specific IgG and IgA are detected in secretions of children following immunization with the group b polysaccharide conjugate vaccine (refs. 24, 63).

Although definitive comparisons have not been made in most cases, existing mouse protection data (refs. 64, 65, 66, 67) suggests that antibodies that can opsonize pneumococci (e.g. those to the capsule) are generally more protective against sepsis than those that block the activities of toxins (e.g. pneumolysin) or enzymes (e.g. autolysin or neuraminidase). However, at the mucosal surface, the role played by antibodies that inactivate toxins and enzymes may be greater than that played by opsonic antibodies. The reason to suspect this is that for opsonic antibodies to exert their anti-bacterial effect, complement and phagocytes are required. Phagocytes are rare on the surface of normal nasopharyngeal tissue, and even if present, the phagocytes do not have the filtering action of the spleen and reticuloendothelial system to increase their chance of interactions with opsonized bacteria. Antibodies that block the virulence enhancing effects of pneumolysin and pneumococcal enzymes should able to bind their antigens just as effectively whether phagocytes were present or not.

The results provided herein show that i.n. immunization with heat-killed pneumococci, and pneumococcal lysates, and purified PspA can protect mice against nasopharyngeal carriage. As noted earlier, the ability of a vaccine to protect against colonization means that it may protect against disease not only in the immunized host, but, by eliminating carriage among immunized individuals, the pathogen and hence any disease it causes may be eliminated from the population as a whole.

The vaccine composition which is administered intranasally as provided herein may be formulated in any convenient manner and in a dosage formulation consistent with the mode of administration and the elicitation of a protective response. The quantity of antigen to be administered depends on the subject to be immunized and the form of the antigen. Precise amounts and form of the antigen to be administered depend on the judgement of the practitioner. However, suitable dosage ranges are readily determinable by those skilled in the art and may be of the order of micrograms to milligrams. Suitable regimes for initial administration and booster doses also are variable, but may include an initial administration followed by subsequent administrations.

EXAMPLES

Example 1

This Example illustrates the provision of a model for pneumococcal carriage in mice.

Seven different strains of S. pneumoniae were inoculated in 10 μl volumes with log-phase cultures in the nares of CBA/N XID mice over a period of several minutes using slow delivery from a 20 μl Pipetman. After 6 to 7 days, the mice were sacrificed and their trachea was cut just below the larynx. 50 μl of sterile saline was instilled and washed out through the nares. The area washed represents the pharynx and nasal tissues. Six of these strains was able to establish carriage without concomitant sepsis or bacteremia. One of the seven strains, (A66, a virulent capsular type 3 strains) killed all four of the i.n. infected CBA/N mice within 3 days. The results are shown in the following Table I:

TABLE I

Carriage of S. pneumoniae in CBA/N (XID) mice: $10^7$ CFU i.n.

| Strain | Capsular type | Log $LD_{50}$ i.v. | Alive: Dead | % With Carriage | Median CFU in nose | Max. CFU/ 50 μl blood |
|---|---|---|---|---|---|---|
| A66 | 3 | <2 | 0:4 | — | — | — |
| BG9739 | 4 | <2 | 3:1[a] | 67[a] | 1,000 | <3 |
| L82106 | 6B | ≧7 | 6:0 | 100 | 2,000 | <3 |
| BG9163 | 6B | 3.5 | 2:0 | 100 | 2,000 | <3 |
| TJ0893 | 14 | .4 | 4:0 | 100 | 4,000 | <3 |
| L82013 | 19 | ≧2 | 4:0 | 100 | 200 | <3 |
| BG8826 | 23F | ≧2 | 2:0 | 100 | 20,000 | <3 |

Note:
Carriage and blood CFU determined after 7 days. Greater than 10 CFU of pneumococci were recovered from the nose of all mice judged as carriers.
[a]One mouse in this group that grew out a contaminant in large numbers and no pneumococci. It seems likely that the contaminant excluded the pneumococci.

Example 2

The procedure of Example 1 was repeated by inoculating the nares of BARB/By mice with two of three pneumococcal isolates used. Carriage was observed with all three strains, without bacteremia or sepsis. The results are shown in the following Table II:

TABLE II

Carriage of *Streptococcus pneumoniae* isolates in BALB/ByJ mice

| Strain | Capsular type | Log LD$_{50}$ i.v. | Alive: Dead | % With Carriage | Median CFU in nose | Max. CFU in 50 µl of blood |
|---|---|---|---|---|---|---|
| D39 | 2 | 7 | 4:0 | 100 | 400 | <3 |
| A66 | 3 | 4 | 4:0 | 100 | 4,000 | <3 |
| BG7322 | 6B | −7 | 4:0 | 75 | 1,700 | <3 |
| L82013 | 19 | ≧8 | 4:0 | 100 | 6,000 | <3 |
| BG8826 | 23F | ≧8 | 4:0 | 75 | 1,900 | <3 |

Note:
Carriage and blood CFU determined after 7 days.
Note:
CFU in nose expressed as CFU in 50 µl of 1 ml nasal wash

Example 3

This Example shows the effects of i.n. inoculation on lung infection.

With three of the strains examined for carriage in Example 1, the numbers of pneumococci in the lung were examined at the time of sacrifice. The results obtained are shown in the following Table III:

TABLE III

Carriage of Three Strains of *S. pneumoniae* in the Nasopharynx of CBA/N Mice

| Strain | L82106 | | BG9163 | | BG8826 | |
|---|---|---|---|---|---|---|
| Capsule Type | 6B | | 6B | | 23F | |
| LD$_{50}$(i.v.) | ≧10$^7$ | | 3 × 10$^3$ | | ≧10$^7$ | |
| Mouse | #1 | #2 | #1 | #2 | #1 | #2 |
| Nasal | 6,600 | 1,400 | 1,500 | 3,300 | 32,000 | 10,000 |
| Blood | <3 | <3 | <3 | <3 | <3 | <3 |
| Lungs | 600 | <60 | <60 | <60 | <60 | 180 |

The data shown in this Table III illustrates the fact that, although the carried pneumococci do not generally cause detectable bacteremia or sepsis, they can spread in at least small numbers to the lung. The ability of *S. pneumoniae* to spread from the nasopharynx to the lung emphasizes the importance of a vaccine blocking carriage in the upper airways.

Example 4

This Example shows the effect of i.n. inoculation on colonization stability.

Colonization appeared to be present for at least 19 days and stable for at least 6 days, as shown by the results in the following Table IV:

TABLE IV

CFU recovered from the nasopharnyx of mice infected i.n. wilh 10$^7$ strain L82106

| | Experiment #1 (day and mouse #) | | | | | | Experiment #2 (day and mouse #) | | | | | |
|---|---|---|---|---|---|---|---|---|---|---|---|---|
| | Day 1 | | Day 3 | | Day 6 | | Day 14 | | | Day 19 | | |
| Source | #1 | #2 | #1 | #2 | #1 | #2 | #1 | #2 | #3 | #1 | #2 | #3 |
| Nasal Wash | 56,862 | 5,346 | 29,160 | 6,336 | 41,365 | 9,504 | 202 | <3 | 261 | 67 | 760 | 124 |
| Blood | <20 | 1,782 | <20 | <20 | <20 | <20 | <3 | <3 | <3 | <3 | <3 | <3 |
| Lungs | <20 | 1,920 | <20 | <20 | <20 | <20 | n.d. | n.d. | n.d. | n.d. | n.d. | n.d. |

Note:
Data expressed as CFU in the 50 µl nasal wash, in the 1 ml of lung homogenate, or in 50 µl of blood.
Since mice were killed to obtain the nasal wash, different mice were assayed at each time point.

To identify the pneumococci from nasal washes in the experiments reported in Examples 1 to 4, they were plated on gentamicin plates since this antibiotic does not kill pneumococci but kills most other bacterial from the nose (ref. 68). Individual colonies from each nasal wash were then picked and replated with an optochin disk to confirm that they were pneumococci. In some cases, the bacteria were capsule-typed to be sure that they were, in fact, the same bacteria with which inoculated the mice were inoculated. Control mice that received no bacteria yielded no bacteria that grew on 0.02% gentamicin and were sensitive to optochin. Subsequent studies have shown that challenge with as few as 2×10$^7$ colony forming units (CFU) also yields carriage in all mice. Lower doses down to 10$^3$ CFU yield comparable carriage in most mice but as many as ¼ to ⅓ of the mice fail to carry any pneumococci after 1 week. These studies indicate that the ideal dose is probably between 10$^7$ and 10$^6$ CFU of L81905.

Example 5

This Example illustrates elicitation of protection against carriage by immunization with heat killed pneumococci and with a lysate of pneumococci.

CBA/N mice were immunized i.n. with 2×10$^7$ heat-killed (60° C.) L82016 or a lysate of an equal number of L82016. Mice were given three i.n. immunizations spaced 10 days apart. The first two injections were given with 5 µg of CTB. Two weeks after the last injection the mice were challenged with $10^8$ CFU of live L82016. The results obtained are set forth in the following Table V:

TABLE V

Elicitation of protection against carriage by immunization with heat killed and autolysed pneumococci

| Immunogen | CFU from individual mice | Geometric mean CFU | P vs CTB | P vs none |
|---|---|---|---|---|
| Heat killed L82016 + CTB | <3, <3, 3, 9, 26 | 4.8 | <.01 | <.02 |
| Autolysed L82016 + CTB | <3, <3, <3, 8, 30 | 4.5 | <.01 | <.02 |
| CTB | 9, 160, 197, 248, 741 | 139 | n.s. | n.s. |
| None | 6, 1340, >1400, >1400 | >354 | n.s. | n.s. |

P. values calculated by Student's t-test.
n.s. = not significantly different.

Example 6

This Example illustrates protection against carriage by immunization with isolated and purified PspA.

CBA/N mice at 10 weeks of age were immunized i.n. with PspA purified by passage over a choline-Sepharose column and eluted in 2% choline chloride. The material run over the column is clarified medium from a pneumococcal culture grown to late log phase in a defined medium (Rijn et al, Infect. Immun. 1990, 27, pp 444–448), containing 0.03% ethanolamine and no more than 0.000,001% choline chloride. When pneumococci is grown in this medium, about half of the PspA is released from the cell surface and can be recovered in the medium. Most pneumococci can not grow in this medium and must be adapted by growing them is CDM with successive lower concentrations of choline. The PspA eluted from the column comprised at least 99% of the eluted protein.

The CBA/N mice were immunized i.n. with 150 ng or s.c. with 1 μg of ≧299.9% pure PspA from strain L82016. Three i.n. immunizations were given at 10 day intervals. 5 μg of commercially-obtained ≧99.9% pure (OTB) (List Biochemical Labs, Inc., Campbell, Calif.) were given with the first two injections as an adjuvant. In the case of s.c. immunization, the first injection was given with PspA in Freund's complete adjuvant and a second injection of PspA in saline was given two weeks later. Two weeks after the last injections, the mice were inoculated i.n. with $10^7$ CFU of L82016. Seven days later, the mice were sacrificed, bled and assayed for carriage in the nasopharynx. The results obtained are illustrated in the following Table VI:

TABLE VI

Intranasal immunization with isolated PspA elicits protection against carriage in CBA/N mice challenged i.n. with $10^7$ CFU of L82016

| Immunization | | Carriage | | |
|---|---|---|---|---|
| Immunogen | Route | Yes: No (≦3 CFU: ≦3 CFU) | Log mean CFU (S.E. factor) | P vs. PspA + CTB |
| PspA | i.n. | 4:0 | 440 (x/+2.6) | 0.014 |
| PspA + CTB | i.n. | 0:4 | <3 | — |
| CTB | i.n. | 8:0 | 440 (x/+⅔) | 0.002 |
| PspA + CFA | s.c. | 4:0 | 240 (x/+⅛) | 0.014 |
| CFA | s.c. | 4:0 | 190 (x/+1.6) | 0.014 |
| None | None | 4:0 | 1260 (x/+4.4) | 0.014 |

P values calculated by Fisher exact test. A one way ANOVA gave a P value of 0.02.

None of the mice exhibited detectable pneumococci in their blood at the time of assay. As may be seen from Table VI, carriage was seen in all mice except the group of four immunized i.n. with PspA and CTB. Control mice immunized with CTB or PspA alone still exhibited carriage.

In another experiment mice were infected i.n. with ten times the dose ($10^8$ CFU), and immunization with PspA+ CTB still protected against pneumococcal carriage (Table VII below). In that experiment the control mice were injected with CTB plus a comparable preparation from a PspA- strain WG44.1, made by the identical purification procedures used for PspA. Mice were immunized with a dilution of the WG44.1 material comparable to that of the isolated PspA. The failure of these control mice to be protected against carriage makes it clear that the protection elicited by isolated PspA is due to PspA and not an undetected contaminant co-isolated with PspA.

When mice were immunized s.c., although they produced humoral antibody to PspA, they still exhibited carriage.

TABLE VII

Intranasal immunization with isolated PspA elicits protection against carriage in CBA/N mice challenged i.n. with $10^8$ CFU of L82016

| Immunogen | CFU from individual mice | Geometric mean CFU | P vs PapA- | P vs pooled controls |
|---|---|---|---|---|
| FL-L82016 PspA + CTB | <3, <3, <3 | <3 | 0.028 | <0.0001 |
| PspA- (WG44.1) + CTB | 128, 18, 277, 49, 527 | 4,875 | — | — |
| CTB | 1,059, 26,720, dead[1] | 11,226 | — | — |
| None | 426, 11,484, dead[1] | 6154 | — | — |

P. values calculated by Welch's t-test.
n.s. = not significantly different.
[1]for the purpose of the statistical calculations, these two mice were assigned carriage values of 50,000 since 49,000 was the highest carriage level observed in a live animal.

Example 7

This Example illustrates the elicitation of secretory and systemic immune responses by i.n. immunization with PspA.

Using the immunization protocol of Example 6, further immunization studies were carried out and mice were bled 10 days after immunization. Secretory and systemic antibody responses were determined and the results appear in the following Table VIII:

TABLE VIII

Antibody to PspA elicited by s.c. and i.t. immunization with PspA

|  |  | Serum |  | Salivary IgG |  |
|---|---|---|---|---|---|
| Antigen | Route | IgM µG | IgG µg | % specific | IgA % specific |
| PspA + CTB | i.n. | <1.5 | 33 ± 14 | 8.7 ± 3 | 13.5 ± 2.6 |
| PspA | i.n. | <1.5 | <1.5 | n.d. | n.d. |
| WG44.1 + CTB | i.n. | <1.5 | <1.5 | <2 | <2 |
| CTB | i.n. | <1.5 | <1.5 | <2 | <2 |
| PspA + CFA | s.c. | <1.5 | 470 ± 217 | n.d. | <2 |
| CFA | s.c. | <1.5 | 1.5 | n.d. | <2 |

Note:
Salivary responses are expressed as percent of total immunoglobulin that is specific to PspA.

As may be seen from this Table, the immunization elicited detectable salivary IgG and IgA antibody responses. Control immunizations with CTB, CFA or a PspA⁻ fraction isolated from PspA⁻ strain WG44.1 did not elicit antibody to PspA. Antibody was not detected when CTB was not used as an adjuvant for i.n. immunization. Assays for antibody to PspA were conducted with ELISA plates coated with isolated PspA.

Example 8

This Example illustrates elicitation of cross-protection against carriage with strains whose PspAs differ from those of immunizing PspA R36A.

Mice were immunized with three i.n. immunizations with 0.15 µg of R36A PspA. In the first two injections immunization was accompanied with 4 µg of purified CTB. Injections were 10 days apart and mice were challenged about 2 weeks after the last immunization. The control mice received the two CTB immunizations and were "immunized" with saline only for the third injection. These mice were largely protected from challenge carriage with two different challenge strains BG7322 and BG8826 of different capsular types and different PspA types. Both have PspA of a different type than the serotype 25 PspA used for immunization. The R36A PspA immunization came from strain R36A which is a non-encapsulated mutant of capsular type 2 strain D39. Thus, neither the capsular type nor the PspA type of the strains providing the immunizing PspA were the same as the challenge strains. Because of the small number of mice in each group the results with the individual strains are not quite significant. However, pooling the data lead to a highly significant demonstration that PspA can elicit protection against challenge pneumococci with a PspA different from the immunizing PspA. The data is summarized in the following Table IX:

TABLE IX

Intranasal immunization with isolated R36A PspA (PspA type 25) elicits cross-protection against carriage in CBA/N challenged i.n. with $10^7$ CFU of strains BG7322 (PspA type 24) and BG8826 (PspA type 20)

| Streptococcus pneumoniae Challenge Strain | | | Immun-ized with | CFU recovered from nasopharynx | | P versus CTB only | Max. CFU/ 50 µl of blood |
|---|---|---|---|---|---|---|---|
| Name | Caps. type | PspA type | | individual mice | median | | |
| BG7322 | 6B | 24 | PspA + CTB | <3, <3, <3, 12 | <3 | 0.057 | <3 |
|  |  |  | CTB | <3, 1500, 1800, 4000 | 1700 |  | <3 |
| BG8826 | 23F | 20 | PspA + CTB | <3, <3, <3, 3 | <3 | 0.057 | <3 |
|  |  |  | CTB | <3, 29, 3700, 5800 | 1900 |  | <3 |
| BG7322 + BG8826 | encap-sulated | not 25 | PspA + CTB | <3, ,3, <3, <3, <3, <3, 3, 12 | <3 | 0.013 | <3 |
|  |  |  | CTB | <3, <3, 29, 1500, 1900, 3700, 4000, 5800 | 1700 |  | <3 |

P value calculated by the Wilcoxon two sample rank test using one degree of freedom.
Note:
CFU in nose expressed as CFU in 50 µl of 1 ml nasal wash.

Example 9

This Example illustrates elicitation of protection against intratracheal (i.t.) challenge by intranasal immunization with PspA.

Whole-length PspA was recovered from *S. pneumoniae* R36A strain (which provides the same PspA as the Rx1 strain). The strain was grown in 100 μl chemically-defined medium (Rijn et al, Infect. & Immun. 1990, vol. 27, pp 444–448), except that the medium contained 0.03% choline chloride. The bacteria were harvested in late log phase (about $5 \times 10^7$ CFU/ml) and washed five times with 20 ml of saline followed by centrifugation at 2000×g for 10 minutes. With each wash, the bacteria was saved and the supernatant discarded. The washed cells then were eluted with 5 ml of 2% choline chloride and the eluted material was shown to contain PspA by dot blot using monoclonal antibody XiR 278.

An identical procedure was carried out on the *S. pneumoniae* strain WG44.1 (McDaniel et al (III)), which does not produce PspA because of the absence of an upstream portion of the pspA gene. This material provided a control in that the preparation should contain the same general impurities that might be in the extract from R36A. The material recovered from the washed WG44.1 cells by elution with 2% choline chloride did not contain detectable PspA by dot blot, as expected.

For the purpose of administration, the PspA preparation from R36A was diluted 1:2. 12 μl of the solution contained 5 μg of added cholera toxin B subunit (CTB) as an adjuvant and was instilled into the nose of each BALB/cJ mouse. Thirty-two and forty-two days later the immunization was repeated in an identical manner. As a control, some mice were immunized with an identical preparation from the WG44.1 *S. pneumoniae* strain. A final group was left unimmunized. Seven days after the third dose, the immunized mice were challenged with $2 \times 10^6$ CFU ($100 \times LD_{50}$) of A66 *S. pneumoniae* intratracheally.

Activity assays also were performed on sera obtained seven days after the third immunization on separate groups of mice immunized by protocols almost identical to those noted above.

The results obtained are set forth in the following Tables X and XI:

TABLE X

Protection against challenge with $10^6$ A66 after i.n. or s.c. immunization with 150 μg doses of PspA

| Antigen | Immunization Route | Challenge Route | % Alive | Median day of death | P value vs. matched control |
|---|---|---|---|---|---|
| PspA + CTB | i.n. | i.t. | 100 | >16 | >0.0001 |
| PspA only | i.n. | i.t. | 25 | 4 | |
| PspA− + CTB | i.n. | i.t. | 11 | 4 | |
| CTB | i.n. | i.t. | 0 | 4 | |
| None | — | i.t. | 0 | 4 | |
| PspA + CFA | s.c. | i.t. | 80 | >16 | 0.02 |
| CFA | s.c. | i.t. | 0 | 4 | |

P values calculated by the Fisher exact test.

TABLE XI

Intranasal Immunization with Rx1 PspA and Intratracheal Challenge with Capsular Type 3 Strain A66

| Immunogen | Adjuvant | IgG anti-PspA (μg/ml) | Challenge CFU of A66 | CFU/ml at day 3* | Day of* Death |
|---|---|---|---|---|---|
| FL PspA (R36A) | CTB | | $2 \times 10^6$ | $<10^2$ | >12** |
| " | " | 17.8 | " | $<10^2$ | >12 |
| " | " | ±3.3 | " | $<10^2$ | >12 |
| " | " | | " | $<10^2$ | >12 |
| PspA (WG44.1) | CTB | | $2 \times 10^6$ | $2 \times 10^8$ | 3 |
| " | " | ≦0.4 | " | $4 \times 10^5$ | 4 |
| " | " | | " | $4 \times 10^4$ | 4 |
| " | " | | " | $2 \times 10^4$ | 4 |
| Saline | Saline | | $2 \times 10^6$ | N.D. | 4 |
| " | " | ≦0.4 | " | N.D. | 4 |
| " | " | | $2 \times 10^5$ | N.D. | 4 |
| " | " | | " | N.D. | 5 |

**FL-PspA vs. Saline (or WG44.1) at P < .005
*Results with individual mice

As can be seen in Table X, 24 hours after infection the unimmunized and the mock immunized mice had high levels of pneumococci in their blood. These mice all died on day 3 post challenge. The mice immunized with PspA exhibited no detectable pneumococci on day 3 and all survived infection. Although the data clearly indicate that i.n. immunization with PspA can protect against pulmonary challenge, the strains of *S. pneumoniae* used, survives well in blood and causes rapid death in mice when injected i.v. ($LD_{50} < 10^2$). Thus, the protection against death may have been due to protection against sepsis as well as pulmonary infection protection had been elicited in the lung.

Example 10

Mucosal immunization with R36A PspA can provide protection against intratracheal and systemic (intravenous) challenge with capsular type 3 A66 *Streptococcus pneumoniae*.

BALB mice were immunized i.n. three times with 150 ng of PspA at 10 day intervals. With each injection they also received 5 μg of purified CTB. The last immunization was given in saline. Control mice received the two CTB injections but no PspA. Four weeks after the last injection the mice were challenged with strain A66 type 3 *S. pneumoniae* by the i.t. or i.v. route at the doses indicated in Table XII. We observed that i.n. immunization could protect against systemic infections by both the i.t. and i.v. route of challenge. In the case of the i.t. route, the immunization protected against the fatal effects of pulmonary infections and probably also sepsis. In the case of the i.v. infection where the pneumococci are injected directly into the blood, the immunization protected against sepsis.

Example 11

BRIEF DESCRIPTION OF DRAWINGS

FIG. 3 (Sequence ID No. 2) is the DNA sequence of the pspA gene with deduced amino acid sequence (Sequence ID No. 3) for the PspA protein;

FIG. 4 (Sequence ID No. 4) depicts the restriction map of pspA (FIG. 4A) and the use of insertion-duplication mutagenesis to construct mutations in the pspA gene (FIG. 4B), FIG. 5 shows the deduced amino acid sequence for the N-terminal region of PspA and the general location of epitopes recognized by monoclonal antibodies;

FIG. 6 shows antibody reactivity with PspA fragments produced by various pspA gene segments.

GENERAL DESCRIPTION

According to one aspect of the present invention, there is provided a purified immunoprotective pneumococcal surface protein, comprising a truncated form of PspA which contains the immunoprotective epitopes of the protein and up to about 90% of the whole PspA protein and from which the functional cell membrane anchor region is absent.

Through the technique of insertion-duplication mutagenesis of the pspA gene of the strain Rx1 of *Streptococcus pneumoniae* with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 *S. pneumoniae*, demonstrating for the first time that a purified PspA can elicit protection and that this truncated segment of the protein contains protective epitopes of PspA.

Figures 1, 2:
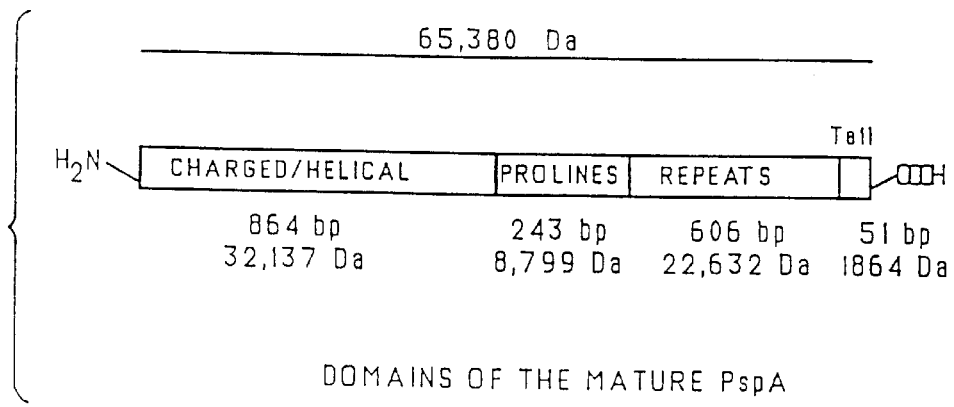
FIG. 1 is a schematic representation of the domains of the mature PspA.
FIG. 2 (Sequence ID No. 1) is the N-terminal amino acid sequence of PspA, wherein bold upper case letters denote charged hydrophilic amino acids, lower-case letters designate apolar, hydrophobic residues, and underlined bold lower case letters denote uncharged, polar, hydrophilic residues.

Amino acid sequence information was obtained on the N-terminal 45 amino acids of the truncated segment of PspA. This sequence is shown in FIG. 2. Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2). In PspA, the periodicity begins with residue 8 and extends throughout the entire sequence, for nearly eleven turns of the helix. Positions "a" and "d" are occupied by apolar amino acids and position "b", "c" and "f" generally contain hydrophilic amino acids. Position "f" is predominantly occupied by lysine. Having regard to these observations, this region of PspA is very likely in an alpha-helical coiled-coil configuration. The deduced amino acid sequence for the whole of the α-helical coiled-coil region is shown in FIG. 5.

We also have cloned and sequenced the entire coding region of pspA (see FIG. 3). The deduced amino acid sequence for the PspA protein reveals three distinct regions of the PspA molecule, shown schematically in FIG. 1. Accordingly, a further aspect of the present invention, there is provided a biologically-pure recombinant DNA molecule coding for the PspA protein or portions thereof and having a coding sequence included within set forth in FIG. 3 or having substantial homology thereto.

The DNA sequence of the pspA gene is contained on a HindIII—KpnI fragment that is 2086 base pairs in length. The pspA gene itself represents approximately 1985 base pairs of this fragment, and comprises an initial region containing transcription and translational signals with translation starting at the ATG/met (nucleotide position 127, codon position −31), followed by a leader sequence extending from the AAG/met (nucleotide position 127, codon position −31) to CGA/ala (nucleotide position 217, codon −1). Mature Pspa starts with the glu amino acid at nucleotide position 220 (codon +1) and ends at the translational stop TAA/OCH at nucleotide position 1984. This translational stop codon is followed by transcription termination signals.

The amino terminal of the protein sequence, predicted from the DNA sequence of FIG. 3, contains a 31 amino acid leader sequence and a 45 amino acid sequence identical to the 45 amino acid sequence of the N-terminal of PspA (FIG. 2). The amino end of the predicted protein sequence is highly charged and α-helical in nature. This region has homology with tropomyosin at the amino acid level (approximately 22% identity and 50% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule. The amino acid sequence of the whole of the α-helical coil region is shown in FIG. 5.

Following the charged helical region is a proline-rich region in which 23 of 81 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of *S. pneumoniae* lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIG. 4. Expression of the same truncated construct (with the pneumococcal promoter) in *E. coli* results in the same PspA fragment being secreted into the periplasm of *E. coli*. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein.

In this procedure, the solution containing PspA is dialyzed to pH6 in 0.02 M salt solution and passed over the resin. The PspA is eluted from the resin with a gradient of 0.08 to 2.0 M ionic strength and is collected in the fraction between 0.34 and 0.87 M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small quantities of PspA are being handled. As an alternative, more suited to large-scale production, the protein may be purified by size chromatography in a pH7 phosphate buffer.

Since it is possible to obtain expression of the truncated form of PspA into the culture medium, as opposed to it being trapped within the cell wall and making purification much more complicated, it is possible to isolate other proteins that have been cloned into the truncated pspA gene by making fusion proteins between PspA and other proteins. Such a technique may be employed to enhance the immunogenicity or preserve the immunogenic structural conformation or presentation of the gene product, to permit the fusion protein to be used in immunization, which may be systemic and/or mucosal, against disease.

One example of such a fusion protein is a fusion of the soluble N-terminal region of PspA and the B-subunit of cholera toxin. Fusion proteins also may be formed by chemical attachment of the truncated PspA protein to other proteins.

Another aspect of the present invention, therefore, provides a method for the production of cloned proteins, which comprises fusing a pspA gene coding for a truncated form of PspA protein with the gene coding for another protein to form a fusion protein clone, transforming *S. pneumoniae, E. coli* or other bacteria with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci, for example, *S. pneumoniae,* and mycobacteria, for example, Bacille Calmette-Guerin (BCG). This approach overcomes the problems inherent in the production of proteins in gram negative bacteria, such as *E. coli,* usually used for cloning, in particular the need to purify the recombinant proteins from endotoxin and the toxicity of many gram positive DNA sequences in gram negative organisms.

For the expression of a fusion protein comprising the soluble N-terminal region of PspA and the B-subunit of cholera toxin (CTB), a gene fusion of a pspA gene coding for a truncated form of PspA protein with a ctxB gene coding for the B-subunit of cholera toxin is effected. Following expression of the fusion protein, the PspA and CTB may be cleaved one from another by dilute acid at an asparagine-proline sequence, known to be labile to dilute acid, engineered at the fusion site of the two proteins.

CTB is known to be highly specific for monosinlogan-glioside ($G_{M1}$). Accordingly, the fusion PspA-CTB protein may be isolated from the culture medium by adsorption to a $G_{M1}$ affinity column, from which the fusion protein subsequently may be eluted at low pH.

The PspA-CTB fusion protein finds considerable utility in solid phase immunoadsorbant assays. By using the fusion protein, it is possible to coat solid supports, such as microtitration plates, with PspA fragments without having first to isolate the PspA fragments. This may be done by adding bacterial extract containing the fusion protein to plates coated with $G_{M1}$. The PspA-CTB fusion protein then binds to $G_{M1}$ through the CTB moiety, thereby coating the solid support with PspA. The resulting coated product then may be used in a solid phase immunoadsorbant assay for the detection of PspA antibody and/or antigen in test samples. Such immunoadsorbant assays constitute an additional aspect of this invention.

The PspA attachment/anchor region, containing the proline-rich region, the repeat region and/or the C-terminus of PspA, also may be employed to effect expression of heterologous proteins in pneumococci, or other gram positive or gram negative bacteria in the which the attachment/anchor region is functional. Generally, expression is effected on bacterial membrane, cell walls or cell surfaces in gram positive bacteria and in the periplasm of gram negative bacteria. An example of such heterologous protein is the B-subunit of cholera toxin.

As mentioned above, the truncated form of PspA provided herein contains the immunoprotective epitopes of the protein and hence is useful in a vaccine against pneumococcal infection. Accordingly, a yet further aspect of the present invention provides a vaccine against pneumococcal infection comprising, as an immunogenically-active component, the purified immunoprotective pneumococcal surface protein provided herein. The PspA protein may be employed as one component of a multicomponent vaccine which is effective in providing protection from a variety of infections.

In addition, gram positive bacteria which have been transformed to express the DSDA gene coding for the truncated soluble PspA protein may be employed, in a live-attenuated or killed form, as an immunologically-active component of a vaccine against pneumococcal infection. In the transformed bacterium, such pspA gene may be fused to a gene coding for another protein. Accordingly, an additional aspect of this invention provides a vaccine against pneumococcal infection comprising, as an immunologically-active component, a live-attenuated or killed bacteria containing a gene coding for the truncated form of PspA.

The truncated form of PspA also may be employed in conjugates with normally weakly-immunogenic or non-immunogenic protection-eliciting molecules, such as various polysaccharides, to achieve immunogenic potentiation thereof. An additional aspect of the invention, therefore, provides a vaccine comprising, as an immunogenically-active component, a conjugate of the purified immunoprotective pneumococcal surface protein provided herein and a normally weakly-immunogenic or non-immunogenic protection-eliciting molecule.

Conserved sequences of pspa, particularly those in the proline-rich and/or repeat regions of the gene, may be employed as probes to detect the presence of pneumococci of various strains, through detection of pneumococcal DNA, in tissues, body fluids and/or secretions. Similarly, portions of the pspA gene may be used in diagnostic kits for the detection of pneumococcal infections.

In addition, primers made based on conserved sequences of pspA, particularly those in the proline-rich and/or repeat regions, may be used to assay for the presence of pneumococci in tissues, body fluids and/or secretions, through amplification of pneumococcal DNA. In this regard, a single primer pair derived from the nucleotide sequence of the pspA gene of *S. pneumoniae* may be employed in an assay using the polymerase chain reaction (PCR) for the specific detection of Streptococcus pneumoniae.

Specific amplification has been achieved of a 678 base pair DNA fragment from S. pneumoniae strain Rx1. After 30 cycles of amplification, the amplimer was detectable by agarose gel electrophoresis. The fragment was successfully amplified in all 32 strains of S. pneumoniae tested. PCR DNA amplification was able to detect less than an estimated 20 ficograms total genomic pneumococcal DNA.

Primers LSM1 and LSM2, having the nucleotide sequences:
LSM1 5'-CCGGATCCAGCTCCTGCACCAAAAC-3'
LSM2 5'-GCGCTGCGACGGCTTAAACCCATTCACCATTG G-3'
amplified the 678 base pair product from pspA from nucleotides 1312 to 1990 of the Rx1 pspA sequence (FIG. 3).

The PCR analysis using the primers described herein is performed in accordance with conventional PCR techniques, such as are described in the literature, for example, as described in Arnhem et al at C&EN Special Report, 36, Oct. 1, 1990. For detection purposes, the primer may be labelled or labelled nucleotide triphosphates may be included in the PCR reaction to label the PCR amplification product.

The PCR primers may be prepared by well-known methods, for example, by oligonucleotide synthesis or by fragmentation of a larger nucleotide sequence using suitable restriction enzymes.

The ability to use a single primer capable of detecting a large number of S. pneumoniae strains enables a universal PCR detection kit to be provided which is able to diagnose pneumococcal infection in mammals, including humans, independent of the strain which has caused the disease.

Example 11.1

This Example illustrates the preparation and growth of novel strains of S. pneumoniae.

The S. pneumoniae strain Rx1, which is a non-encapsulated derivative of capsular type 2 strain D39 (National Collection of Type Cultures, London, NCTC #7466), was subjected to insertional inactivation (as described in McDaniel et al (III) 1987, Crain et al 1990, Talkington et al 1991, with 10 different cloned fragments of PspA (see FIG. 4). These fragments have all been obtained from restriction digests of cloned PspA DNA on a plasmid in E. coli strain JY4313 (deposited with the American Type Culture Collection on Jan. 31, 1991 under ATCC accession number 68529). This insertional duplication mutagenesis (see FIG. 4) results in the termination of gene expression near the 3' end of the cloned fragment.

One of the resultant strains, JY2008 (deposited with the American Type Culture Collection on Jan. 24, 1991 under accession number 55143), which was produced by a fragment of DNA encoded in pKSD300 (McDaniel et al (III) 1987), produces a PspA fragment of 27 kDa (apparent molecular weight 43 kDa). This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then may be isolated from culture supernatants, as described below.

Figure 7:
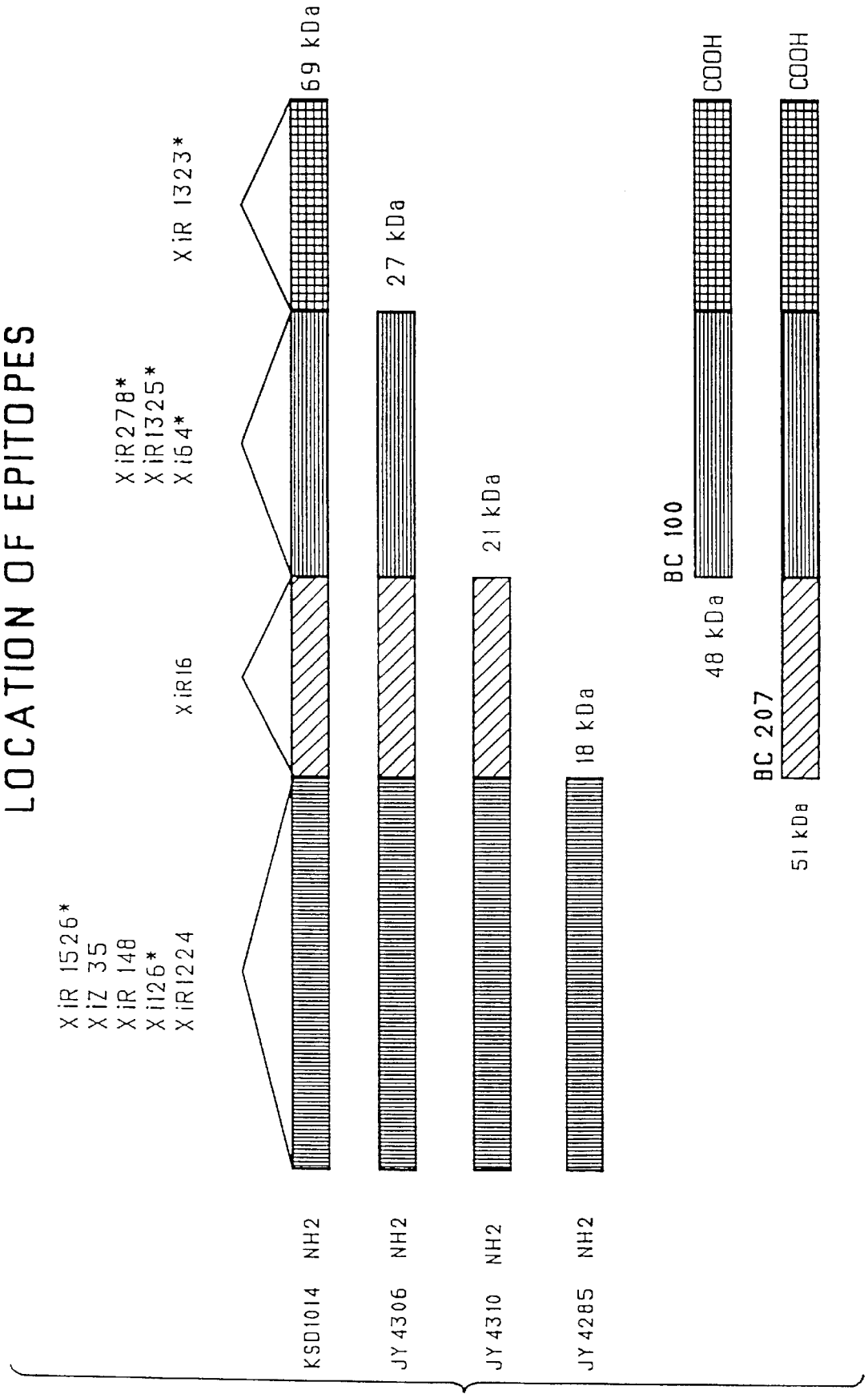
FIG. 7 shows the mapped location of epitopes in the PspA fragments produced by the different pspA gene segments.

By directing the insertion to different points in the pspA gene, different lengths of truncated, non-attached PspA protein derivatives can be produced, as seen in FIG. 7.

STRAINS, PLASMIDS AND PROBES

In the Examples which follow as well as in the accompanying drawings, reference is made to certain plasmids and bacterial strains transformed by such plasmids as well as vector DNA segments, some of which have been deposited with ATCC and all of which are fully described herein. The following Tablet III provides a summary of such materials.

TABLE 11.II

| Identification | Type | Description | Deposit | Location |
|---|---|---|---|---|
| JY4313 | E. coli strain | PspA DNA | ATCC 68529 | FIG. 1 |
| JY2008 | S. pneumoniae strain | PspA fragment 43 kDa | ATCC 55143 | FIG. 1 |
| JY4306 | E. coli strain | PspA fragment 43 kDa | ATCC 68522 | FIG. 3 |
| JY4310 | | PspA fragment 21 kDa | None | FIG. 7 |
| JY4285 | | PspA fragment 18 kDa | None | FIG. 7 |
| pJY4163 | Plasmid | Expression plasmid used for expression of PspA –CTB fusion protein (29 kDa) | None | FIG. 6 |
| JY4323 | DNA probe | HindIII-KpaI segment | None | FIG. 8 |
| JY4306 | DNA probe | HindIII-Dra-I segment | None | FIG. 8 |
| JY4262 | DNA probe | BclI-Bst-NI segment | None | FIG. 8 |

The pneumococcal strain JY2008 was grown in 6 liters of a chemically defined medium (see Inf. Imm. 27:444) supplemented with 0.10% choline chloride, 0.075% L-cysteine hydrochloride and 0.25% NaHCO$_3$. The supernatant fluid of the mid-log phase culture of JY2008 was harvested using a 0.22 μm membrane tangential flow filter and concentrated 60 fold.

Introduction of the plasmid pKSD300 into the unmodified D39 strain similarly yielded the 43 kD truncated PspA protein. Introduction of the plasmid pKSD300 into the type 3 S. pneumoniae strain WU2 (PspA protein approximately 92 kD) yielded, upon growth of the organism, a non-attached truncated PspA protein of approximately 46 kD molecule size.

Example 11.2

This Example illustrates the purification of PspA.

The concentrated supernatant fluid, produced as described in Example 1, was washed in 0.1 M PBS, pH 7.2, and ultracentrifuged at 196,000xg. The supernatant fluid was diluted 1:5 in 20 mM L-histidine buffer-NaCl, the pH adjusted to 6.0 and the injected into a DEAE-fibered Isonet-D2 an ion exchange column.

A stepwise NaCl gradient from 80 mM to 2 M was applied to the column and PspA-containing fractions (0.32 to 0.64 M ionic strength) were pooled and separated on an SDA-polyacrylamide gel. The proteins on a representative section of the gel were stained with Comassie Blue R-250 to identify PspA. The fraction containing PspA was excised from the remainder of the SDS-gel and electroeluted from the excised gel. The eluted protein was precipitated in a 50:50 methanol:acetone solvent and resuspended in PBS. Purity of product was confirmed by silver staining and Western Immunoblotting with mAb Xil26 (IgG 2b, k, see McDaniel et al (I), supra).

Example 11.3

This Example illustrates the isolation of PspA from the periplasmic space of *Escherichia coli*.

Isolation from the periplasmic space of *E. coli* was accomplished by standard techniques. *E. coli* strain JY4306 (which produces the 43 kDa N-terminal fragment of PspA, the amino acid sequence of which is shown in FIG. 3. This strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were spun at 400×g for 10 minutes at 0° C. All supernatant was removed from the pellet and the pellet was resuspended rapidly in about 100 volumes of 4° C. water. After 10 minutes the suspension was centrifuged at 4,000×g for 10 minutes at 4° C. The pellet was discarded and the supernatant, which contained the PspA was saved. Concentration of the supernatant was by standard procedures such as concentration against solid sucrose or ultrafiltration. Purification of the protein isolated from *E. coli* proceeded by the same chromatography techniques used for the isolated of the 43 kDa (truncated) PspA from the media of growing pneumococci.

Example 11.4

This Example illustrates the immunogenic properties of the PspA protein.

Sixteen 7-week old CBA/N mice carrying the Xid mutation (Jackson Laboratories, Bar Harber, Me.) were bled via the periorbital sinus to establish pre-exposure levels dt antibody to PspA. Purified PspA, prepared as described in Example 11.2, was emulsified in complete Freund's adjuvant and injected subcutaneously into the inguinal and axillary regions, delivering approximately 5 $\mu$g of protein per mouse. Fourteen days later, the mice were injected intraperitoneally with 5 $\mu$g of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 11.1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr, washed and incubated with Strepavidin-conjugated phosphatase. The membranes were developed with 5-bromo-4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge of the eight mice immunized with buffer controls, six were dead by two days post challenge, while the two remaining control mice appeared very sick, with ruffled fur, arched back and decreased movement, two to three days following challenge but survived. Chi-square analysis indicated that there was a significant difference (P<0.003) in survival between the immunized and control groups.

Preimmunization and prechallenge sera were analyzed by Western immunoblotting. None of the preimmunization sera contained antibody to truncated PspA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table 11III:

TABLE 11.III

| Immunogen | Detection of Antibody to PspA | Alive at 2 days post challenge | Alive at 14 days post challenge |
|---|---|---|---|
| Isolated PspA (Example 2) | 8/8 | 8/8 | 8/8 |
| Sterile SDS (control) | 0/8 | 2/8 | 2/8 |

As may be seen from the data in Table III, immunization with two 5 $\mu$g doses of the purified PspA molecule elicited protection against fatal infection of CBA/N mice and elicited antibodies reactive with the PspA of the challenge strain.

Example 11.5

This Example illustrates sequencing of the PspA protein.

Purified PspA, prepared as described in Example 5.2, was electrophoresed through 9% resolving gels containing recrystallized SDS with the Laemmli buffer system (Nature 227:680). The gels were soaked twice in a 10 mM 3-(cyclohexylamino)-1-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A for 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 depicts the N-terminal 45 residue amino acid sequence and FIG. 5 depicts the amino acid sequence for the whole alpha-helical region. The DNA sequence of the whole pspA gene and the deduced amino acid sequence for the PspA protein are shown in FIG. 3.

Example 11.6

This Example illustrates the use of the pspA 5'-sequence and/or the PspA N-terminal region to serve as an expression and leader sequence for expressing and/or excreting/secreting heterologous proteins from *S. pneumoniae* and *E. coli*. In this Example, there is described the expression of the N-terminal of the PspA protein fused to the B-subunit of cholera toxin (CTB) through a genetic fusion and the excretion of the fused protein from pneumococci and its secretion into the periplasmic space of *E. coli*.

A fusion protein consisting of CTB and the N-terminal half of PspA was constructed and expressed in *E. coli*. The HindIII/Dral pspA gene fragment used contained all the pspA transcription and translation initiation signals and the PspA signal peptide leader sequence for transport across the cell membrane. The mature PspA encoded by this fragment is predicted to be a product of 29 kDa (observed molecular weight of 42 kDa), encompassing more than 90% of the α-helical coiled-coil domain. The CTB fragment used lacked transcription and translation initiation signals. Expression from pspA promoter through pspA and then in-frame translational readthrough into the CTB-encoding gene ctxB resulted in production of a 12 kDa CTB product fused to the upstream PspA product. The PspA-CTB fusion protein was stably expressed in both high and low copy number plasmids (pUC18, more than 100 copies/cell; pJY4163, about 15 to 30 copies/cell) in *E. coli.*

The fusion products were of the expected size (about 54 kDa) and reacted with antibody to both PspA and CTB. That the CTB product retained its functionality was demonstrated by the ability of the fusion protein to bind ganglioside $G_{M1}$, a property of CTB.

The high level of expression of the fusion product apparently resulted in a reduced rate of processing and/or conformational changes that prevented the protein from being completely transported to the periplasm. However, in the lower copy number construct, about 60% of the fusion protein was localized in the periplasm, where large quantities were readily released from *E. coli* by osmotic shock.

In addition to expression in *E. coli,* the fusion protein also was expressed in *S. pneumoniae* by transformation of the low copy number construct into the avirulent *S. pneumoniae* Rx1 to generate an insertion-duplication mutant. In this way, the gene encoding the fusion protein was integrated into the *S. pneumoniae* chromosome, from which it was stably expressed. As in the case of Example 1, the truncated PspA molecule lacking the attachment/anchor region, this time in the form of the PspA-CTB fusion protein, was excreted into the culture supernatant. The fusion protein product was of the expected molecular size (54 kDa), reacted with antibody to PspA and CTB, and bound $G_{M1}$.

Example 11.7

This Example illustrates the use of PspA attachment or anchor region to permit expression of heterologous proteins on the surface of *S. pneumoniae* or other bacteria in which the attachment/anchor sequence is functional in particular the expression of a PspA-CTB (cholera toxin B subunit) fusion expressed on the surface of pneumococci.

The N-terminal encoding region of PspA, including its transcription and translation initiation signals and its signal peptide leader sequence, is linked via a translationally in-frame genetic fusion to the CTB-encoding ctxB fragment that lacks transcription and translation initiation and termination signals. This sequence is followed in-frame by the PspA attachment/anchor domain, including part or all of the proline, repeat and C-terminal domains. The resulting fusion protein is directed to the outside of the cell via the PspA leader sequence, which is cleaned following transport across the membrane, and then attached to cell by the PspA attachment/anchor sequence. The heterologous protein, located between the two PspA fragments is expressed on the outside surface of the membrane and, in *S. pneumoniae,* on the surface of the cell.

Example 11.8

This Example illustrates the expression of truncated and full length PspA by the *Mycobacterium tuberculosis* strain Bacille Calmette-Guerin (BCG).

BCG was chromosomically modified to incorporate the pspA gene coding for the truncated PspA protein. The 43 kDa truncated PspA protein was expressed from the modified BCG to approximately 15% of total BCG protein. This result was achieved with an expression vector construct carrying the pspA gene segment encoding the 43 kDa region without its 5'-secretion signal. Expression was only about 1% of BCG protein when the PspA or mycobacterial signal sequences were included. In either case, a significant portion of the expressed PspA was excreted into the medium. Expression of the 43 kDa PspA protein in a fusion with the mycobacterial lipoprotein signal sequence resulted in the expression of the recombinant PspA in the membrane fraction of BCG.

This latter result suggested that the fusion of the lipoprotein signal sequence resulted in acylation of the recombinant PspA. Fluorescent activated cell sorting with fluorochrome-conjugated monoclonal antibodies to PspA demonstrated expression of PspA on the surface of these bacteria.

Example 11.9

This Example illustrates the close homology of portions of the pspA gene among different strains of pneumococci and the potential that such homology may be useful for molecular (DNA) approaches to detect pneumococci in tissues, body fluids and/or secretions and to identify pneumococci grown from patient samples.

Three DNA probes were employed, namely full length pspA, JY4323 (N-terminal HindIII to C-terminal KpnI), the N-terminal half of pspa, JY4306 (N-terminal HindIII to DraI at position 996 (see FIG. 3) and most of the proline and repeat regions, JY4262 (BclI at position 1221 to BstNI at position 1832). Under stringency conditions requiring 95% identity, probes JY4323 and JY4262 reacted with cells of over 200 independent isolates of *S. pneumoniae* by Southern blot.

When the chromosomal DNA was cut with HindIII, there generally was observed that each of these probes detected two discrete bands whose exact size was dependent on the strain examined. In Rx1 pneumococci, the two bands were 4.0 and 9.1 kb. The 4.0 kb band corresponded to pspA and was altered or absent in pspA mutants. The other band shares some homology with the coding regions for both the N-terminal and C-terminal halves of PspA but is not affected by pspA mutations. The JY4323 and JY4262 probes failed to react with another gram positive bacterium, *Streptococcus pyogenes,* and a gram negative bacterium, *Salmonella typhimurium.* The N-terminal probe, JY4306, recognized about one-third of the strains of pneumococci tested.

These results indicate that a sequence included in the proline/repeat region is shared by all strains of pneumococci and apparently not by other bacterial species. Sequences in the N-terminal half of the molecule appear to be more variable.

Example 11.10

This Example illustrates the detection and determination of the location of epitopes in the α-helical N-terminal region of PspA.

Monoclonal antibodies protective against pneumococcal infection in a mouse model, denoted by an asterisk in FIGS. 5, 6 and 7, were used to determine the location of epitopes for each antibody in the α-helical N-terminal region of PspA. The sites were mapped to fragments of PspA. The results are illustrated in FIGS. 5 to 7, with FIG. 5 showing the deduced amino acid sequence for the N-terminal region of PspA and the general location of epitopes recognized by monoclonal antibodies, FIG. 6 showing antibody reactivity with PspA fragments produced by various pspA gene segments, and FIG. 7 showing the mapped location of epitopes in the PspA fragments produced by the different pspA gene segments.

Numbers 138, 193 and 261 in FIG. 5 indicate break positions in the PspA fragments used to map the location of epitopes detected by monoclonal antibodies Xi1526, Xi126, XiR35, XiR38, XiR1224, XiR16, Xi64, XiR278, Xi1325 and Xi1323. The asterisk (*) after some of the antibodies denotes those which are able to protect against fatal pneumococcal infection with strain WU2 pneumococci.

In addition, the vertical lines to the right of the Figure indicate those areas predicted to have coiled-coil α-helical structure. The divisions to the left of the Figure indicate the mapped location of the epitopes for each antibody.

SUMMARY OF EXAMPLE

In summary of this disclosure, the present invention relates to a truncated PspA molecule capable of eliciting an immunoprotective response and hence containing the protective epitopes of PspA protein. Modifications are possible within the scope of this invention.

SEQUENCE LISTINGS

Submitted with this application are Sequence Listings, identified as follows:
(a) SEQ ID No: 1 shows the nucleotide sequence and derived amino acid sequence for the HindIII-KpnI fragment containing the complete pspA gene, as shown in FIG. 3.
(b) SEQ ID No: 2 shows the derived amino acid sequence for the PspA protein, as shown in FIG. 3.
(c) SEQ ID No: 3 shows the N-terminal amino acid sequence of PspA, as shown in FIG. 2.
(d) SEQ ID No: 4 shows the derived amino acid sequence for the N-terminal region of PspA as shown in FIG. 5.
(e) SEQ ID No: 5 shows the nucleotide sequence for primer LSM1.
(f) SEQ ID No: 6 shows the nucleotide sequence for primer LSM2.

by pneumococci, by mucosal, particularly intranasal (intranasopharyngeal), administration of PspA in various forms. Modifications are possible within the scope of the invention.

REFERENCES

1. Anonymous. Centers for Disease Control HIV/AIDS Serveillance Report. 1991; August: 1–18.
2. Fraser, D. W. What are our bacterial disease problems. In: J. B. Robbins, Hill, J. C., Sadoff, J. C. ed. Bacterial Vaccines. New York: 1982: xix–xxiv.
3. Berman, S., McIntosh, K. Selective primary health care: stratagies for control of disease in the developing world. XXI acute respiratory infections. Rev. Infect. Dis. 1985; 7: 647–491.
4. Greenwood, B. M., Greenwood, A. M., Bradley, A. K., Tulloch, S., Hayes, R., Oldfield, F. S. J. Deaths in infancy and early childhood in a well vaccinated, rural, West African population. Ann. Trop. Pediatr. 1987; 7: 91–99.
5. Spika, J. S., Munshi, M. H., Wojtyaniak, B., Sack, D. A., Hossain, A., Rahman, M., Saha, S. K. Acute lower respiratory infections: a major cause of death in children in Bangladesh. Ann. Trop. Pediatr. 1989; 9: 33–39.
6. Bale, J. R. Etiology and epidemiology of acute respiratory tract infections in children in developing countries. Rev. Infect. Dis. 1990; 12 (Suppl 8): S861–S1083.
7. Munoz, R., Musser, J. M., Crain, M., Briles, D. E., Marton, A., Parkinson, A. J., Sorensen, U., Tomasz, A. Geographic distribution of penicillin-resistant clones of *Streptococcus pneumoniae:* characterization by penicillin-binding protein profile, surface protein A typing, and multilocus enzyme analysis. Clinic. Infect. Dis. 1992; 15: 112–118.
8. Marton, A., Gulyas, M., Munoz, R., Tomasz, A. Extremely high incidence of antibiotic resistance in clinical isolates of *Streptococcus pneumoniae* in Hungary. J. Infect. Dis. 1991; 163: 542–548.
9. Klugman, K. P. Pneumococcal resistance to antibiotics. Clin. Microbiol. Rev. 1990;
10. Gray, B. M., Converse, G. M. III, Dillon, H. C. Epidemiologic studies of *Streptococcus pneumoniae* in infants: acqusition, carriage, and infection during the first 24 months of life. J. Infect. Dis. 1980; 142: 923–933.

TABLE XII

Intranasal immunization with R36A PspA can protect against systemic infection with S. pneumoniae.

| Challenge | | | Days to Death | | | Survival | |
| --- | --- | --- | --- | --- | --- | --- | --- |
| Route | Log Dose | Immunogen | Individual | Median | P vs. control[1] | Alive: Dead | P vs. control[2] |
| i.t. | 5.1 | PspA + CTB | >21, >21, >21, >21, >21 | >21 | | 5:0 | |
| | | CTB | 3, 3, 4, 4, 4, 5, 6, >21, >21, >21 | 4.5 | 0.02 | 3:7 | 0.02 |
| i.v. | 4.9 | PspA + CTB | >21, >21, >21, >21, >21 | >21 | 0.045 | 5:0 | 0.042 |
| | | CTB | 4, 4, 4, 4, 5, 5, >21, >21, >21, >21 | 5 | | 4:6 | 6 |

[1]calculated by one tailed Wilcoxon two sample rank test.
[2]calculated by one tailed Fisher exact test.

SUMMARY OF THE DISCLOSURE

In summary of this disclosure, the present invention provides a method of preventing colonization of pneumococci in a host and for protecting against systemic infection 11. Gray, B. M., Converse, G. M. III, Huhta, N., Johnston, R. B. Jr., Pichichero, M. E., Schiffman, G., Dillon, H. C. Jr. Antibody response to pneumococcal carriage. J. Infect. Dis. 1981; 142: 312–318.

12. Hendley, J. O., Sande, M. A., Stewart, P. M., al. e. Spread of *Stereptococcus pneumoniae* in families. I. Carriage rates and distribution of types. J. Infect. Dis. 1975; 132: 55.
13. Smillie, W. G., Warnock, G. H., White, H. J. A study of a type I pneumococcus epidemic at state hospital at Worchester, Mass. Am J Pub Hlth 1938; 28: 293–302.
14. Smillie, W. G. A study of an outbreak of type II pneumococcal pneumonia in the Veterans Administration Hospital at Bedford, Mass. Am. J. Hyg. 1936; 24: 522–535.
15. Gratten, M., Naraqi, S., Hansman, D. High prevalence of penicillin-insensitive penumococci in port moresby, Paupa New Guinea. Lancet 1980; ii: 192–195.
16. DeMaria, T. F., McGhee, R. B., Lim, D. J. Rheumatoid factor in otitis media with effusion. Arch. Otolaryngol. 1984; 110: 279–280.
17. Bohr, V., Rasmussen, N., Hansen, B., Gade, A., Kjersem, H., Johsen, N., Paulson, O. Pheumococcal meningitis: An evaluation of prognostic factors in 164 cases based on mortality and on a study of lasting sequelae. J. Infect. Dis. 1985; 10: 143–157.
18. Klein, J. O. The epidemiology of pneumococcal diseases in infants and children. Rev. Infect. Dis. 1981; 3: 246-.
19. Bolan, G., Broome, C. V., Facklam, R. R., Plikaytis, B. D., Fraser, W. D., Schlech, W. F. I. Pneumococcal vaccine efficacy in selected populations in the Unites States. Ann. Intern. Med. 1986; 104:1–6.
20. Shapiro, E. D., Berg, A. T., Austrian, R., Schroeder, D., Parcells, V., Margolis, A., Adair, R. K., Clemmens, J. D. Protective efficacy of polyvalent pneumococcal polysaccharide vaccine. N. Engl. J. Med 1991; 325: 1453–1460.
21. Cowan, M. J., Ammann, A. J., Wara, D. W., Howie, V. M., Schultz, L., Doyle, N., Kaplan, M. Pneumococcal polysaccharide immunization in infants and children. Pediatrics 1978; 62: 721–727.
22. Gotschlich, E. C., Goldschneider, I., Lepow, M. L., Gold, R. The immune response to bacterial polysaccharides in man. Antibodies in human diagnosis and therapy. New York: Raven, 1977: 391–402.
23. Barbour, M. L., Mayon-White, R. T., Crook, D. W., Coles, C., Moxon, E. R. The influence of *Haemophilus influenzae* type b (Hib) conjugate vaccine (PRP-T) on oropharyngeal carriage of Hib in infants under 12 months of age. ICAAC Abstracts 1993; 33: 175.
24. Chiu, S. S., Greenberg, P. D., Marcy, S. M., Wong, V. K., Chang, S. J., Chiu, C. Y., Ward, J. I. Mucosal antibody responses in infants following immunization with Haemophilus influenzae. Pediatric Res. Abstracts 1994; 35: 10A.
25. Fallon, M. T., Reinhard, M. K., Gray, B. M., Davis, T. W., Lindsey, J. R. Inapparent *Streptococcus pneumoniae* type 35 infections in commercial rats and mice. Laboratory Animal Science 1988; 38: 129-.
26. Douglas, R. M., D. H., Miles, H. B., Paton, J. C. Pneumococcal carriage and type-specific antibody Failure of a 14-valent vaccine to reduce carriage in healthy children. American Journal of Diseases of Children 1986; 140: 1183–1185.
27. Douglas, R. M., Miles, H. B. Vaccination against *Streptococcus pneumoniae* in childhood: lack of demonstrable benefit in young Australian children. Journal of Infectious Diseases 1984; 149: 861–869.
28. Mestecky, J. The common mucosal immune system and current strategies for induction of immune response in external secretions. J. Clin. Immunol. 1987; 7: 265–276.
29. Croitoru, K., Bienenstock, J. Characteristics and functions of mucosa-associated lymphoid tissue. In: P. L. Ogra, Mestecky, J., Lamm, M. E., Strober, W., McGhee, J. R., Bienenstock, J. ed. Handbook of Mucosal Immunology. San Diego, Calif.: Academic Press, Inc., 1994: 141–149.
30. Bienenstock, J., Johnston, N., Perey, D. Y. Bronchial lymphoid tissue. I. Morphologic characteristics. Lab. Invest. 1973; 28: 686–692.
31. Bienenstock, J., Johnston, N., Perey, D. Y. Bronchial lymphoid tissue. II. Functional characterisitics. Lab. Invest. 1973; 28: 693–698.
32. Pabst, R. Is BALT a major component of the human lung immune system? Immunology Today 1992; 13: 119–122.
33. Kuper, C. F., Koornstra, P. J., Hameleers, D. M. H., Biewenga, J., Spit, B. J., Duijvestijn, A. M., van Breda Vriesman, P. J. C., Sminia, T. The role of nasopharyngeal lymphoid tissue. Immunol. Today 1992; 13: 219–224.
34. Wu, H-Y, Russell, M. W. Induction of mucosal immunity by intranasal application of a streptococcal surface protein antigen with the cholera toxin B subunit. Infection and Immunity 1993; 61: 314–322.
35. Russell, M. W., Wu, H-Y. Distribution, persistence, and recall of serum and salivary antibody responses to peroral immunization with protein antigen I/II of *Streptococcus mutans* coupled to the cholera toxin B subunit. Infection and Immunity 1991; 59: 4061–4070.
36. Elson, C. O., Ealding, W. Generalized systemic and mucosal immunity in mice after mucosal stimulation with cholera toxin. J. Immunol. 1984; 132: 2736–2741.
37. Elson, C. O. Cholera toxin and its subunits as potential oral adjuvants. Curr. Topics Microbiol. Immunol. 1989; 146: 29–33.
38. Lycke, N., Holmgren, J. Strong adjuvant properties of cholera toxin on gut mucosal immune responses to orally presented antigens. Immunology 1986; 59: 301–308.
39. Wilson, A. D., Stokes, C. R., Bourne, F. J. Adjuvant effect of cholera toxin on the mucosal immune response to soluble proteins. Differences between mouse strains and protein antigens. Scand. J. Immunol. 1989; 29: 739–745.
40. Wilson, A. D., Clarke, C. J., Stokes, C. R. Whole cholera toxin and B subunit act synergistically as an adjuvant for the mucosal immune response of mice to keyhole limpet haemocyanin. Scand. J. Immunol. 1990; 31: 443–451.
41. Lycke, N., Tsuji, T., Holmgren, J. The adjuvant effect of Vibrio cholerae and *E. coli* heat labile enterotoxins is linked to the ability to stimulate CAMP. European Journal of Immunology 1992; 22: 2277–2281.
42. Lycke, N., Karlsson, U., Sjblander, A., Magnusson, K-E. The adjuvant action of cholera toxin is associated with an increased intestinal permeability for luminal antigens. Scandinavian Journal of Immunology 1991; 33: 691–698.
43. Gizurarson, S., Tamura, S., Kurata, T., Hasiguchi, K., Ogawa, H. The effect of cholera toxin and cholera toxin B subunit on the nasal mucosa membrane. Vaccine 1991; 9: 825–832.
44. Bromander, A., Holmgren, J., Lycke, N. Cholera toxin stimulates IL-1 production and enhances antigen presentation by macrophages in vitro. Journal of Immunology 1991; 146: 2908–2914.
45. Anastassiou, E. D., Yamada, H., Francis, M. L., Mond, J. J., Tsokos, G. C. Effects of cholera toxin on human B cells. Cholera toxin induces B cell surface DR expression while it inhibits anti-$\mu$ antibody-induced cell proliferation. J. Immunol. 1990; 145: 2375–2380.
46. Muñoz, E., Zubiaga, A. M., Merrow, M., Sauter, N. P., Huber, B. T. Cholera toxin discriminates between T helper 1 and 2 cells in T cell receptor-mediated activation: Role of cAMP in T cell proliferation. J. Exp. Med. 1990; 172: 95–103.

47. Lycke, N., Strober, W. Cholera toxin promotes B cell isotype differentiation. J. Immunol. 1989; 142: 3781–3787.
48. Wilson, A. D., Bailey, M., Williams, N. A., Stokes, C. R. The in vitro production of cytokines by mucosal lymphocytes immunized by oral administration of keyhole limpet hemocyanin using cholera toxin as an adjuvant. European Journal of Immunology 1991; 21: 2333–2339.
49. Francis, M. L., Ryan, J., Jobling, M. G., Holmes, R. K., Moss, J., Mond, J. J. Cyclic AMP-independent effects of cholera toxin on B cell activation. II. Binding of ganglioside $G_{M1}$ induces B cell activation. Journal of Immunology 1992; 148: 1999–2005.
50. Woogen, S. D., Ealding, W., Elson, C. O. Inhibition of murine lymphocyte proliferation by the B subunit of cholera toxin. Journal of Immunology 1987; 139: 3764–3770.
51. Garrone, P., Banchereau, J. Agonistic and antagonistic effects of cholera toxin on human B lymphocyte proliferation. Molecular Immunology 1993; 30: 627–635.
52. Haack, B. M., Emmrich, F., Resch, K. Cholera toxin inhibits T cell receptor signaling by covalent modification of the CD3-ξ subunit. Journal of Immunology 1993; 150: 2599–2606.
53. Abraham, E., Robinson, A. Oral immunization with bacterial polysaccharide and adjuvant enhances antigen-specific pulmonary secretory antibody response and resistance to pneumonia. Vaccine 1991; 9: 757–764.
54. Szu, S. C., Li, X., Schneerson, R., Vickers, J. H., Bryla, D., Robbins, J. B. Comparative immunogenicities of Vi polysaccharide-protein conjugates composed of cholera toxin or its B subunit as a carrier bound to high- or lower-molecular-weight Vi. Infect. Immun. 1989; 57: 3823–3827.
55. Chen, K-S, Strober, W. Cholera holotoxin and its B subunit enhance Peyer's patch B cell responses induced by orally administered influenza virus: disproportionate cholera toxin enhancement of the IgA B cell response. Eur. J. Immunol. 1990; 20: 433–436.
56. Liang, X., Lamm, M. E., Nedrud, J. G. Oral administration of cholera toxin-Sendai virus conjugate potentiates gut and respiratory immunity against Sendai virus. Journal of Immunology 1988; 141: 1495–1501.
57. Brimblecombe, F. S. W., Cruicshank, R., Masters, P. L., Reid, D. D., Stewart, G. T. Family studies of respiratory infections. British Medical Journal 1958;: 119–128.
58. Masters, P. L., Brumfitt, W., Mendez, R. L., Likar, M. Bacterial flora of the upper respiratory tract in Paddington families, 1952–1954. Brit. Med. J. 1958; 1: 1200–1205.
59. Gwaltney, J. M., Sande, M. A., Austrian, R., al. e. Spread of *Streptococcus pneumoniae* in families: II Relation of transfer of *Streptococcus pneumoniae* to incidence of colds and serum antibody. J. Infect. Dis. 1975; 132: 62.
60. Russell, M. W., Prince, S. J., Ligthart, G. J., Mestecky, J., Radl, J. Comparison of salivary and serum antibodies to common environmental antigens in elderly, edentulous, and normal adult subjects. Aging Immunol. Infect. Dis. 1990; 2: 275–286.
61. Bessen, D., Fischetti, V. A. Influence of intranasal immunization with synthetic peptides corresponding to conserved epitopes of M protein on mucosal immunization by group A streptococci. Infect. Immun. 1988; 56: 2666–2672.
62. Hollingshead, S. K., Simecka, J. W., Michalek, S. M. Role of M protein in pharyngeal colonization by group A streptococci in rats. Infect. Immun. 1993; 61: 2277–2283.
63. Kauppi, M., Eskola, J., Kathty, H. H. influenzae type b (Hib) conjugate vaccines induce mucosal IgA1 and IgA2 antibody responses in infants and children. ICAAC Abstracts 1993; 33: 174.
64. Briles, D. E., Forman, C., Horowitz, J. C., Volanakis, J. E., Benjamin, W. H. Jr., McDaniel, L. S., Eldridge, J., Brooks, J. Antipneumococcal effects of C-reactive protein and monoclonal antibodies to pneumococcal cell wall and capsular antigens. Infect. Immun. 1989; 57: 1457–1464.
65. Briles, D. E., Claflin, J. L., Schroer, K., Forman, C. Mouse IgG3 antibodies are highly protective against infection with *Streptococcus pneumoniae*. Nature 1981; 294: 88–90.
66. Lock, R. A., Paton, J. C., Hansman, D. Comparative efficacy of pneumococcal neuraminidase and pneumolysin as immunogens protective against *Streptococcus pneumoniae*. Microb. Pathog. 1988; 5: 461–467.
67. Lock, R. A., Hansman, D., Paton, J. C. Comparative efficacy of autolysin and pneumolysin as immunogens protecting mice against infection by *Streptococcus pneumoniae*. Microbial Pathogenesis 1992; 12: 137–143.
68. Converse, G. M. III, Dillon, H. C. Jr. Epidemiological studies of *Streptococcus pneumoniae* in infants: methods of isolating pneumococci. J. Clin. Micro. 1977; 5: 293–296.

What we claim is:

1. An aerosolizer for intranasal administration of an immunogenic composition, said aerosolizer containing an immunogenic composition to elicit a protective immunological response against colonization with *Streptococcus pneumoniae* in the nasopharynx, said immunogenic composition consisting essentially of an immunizing amount of *Streptococcus pneumoniae* pneumococcal surface protein A (PspA) in the form of a killed whole *Streptococcus pneumoniae*, a *Streptococcus pneumoniae* lysate, an isolated and purified PspA or an immunogenic fragment thereof containing a protection eliciting epitope; and a pharmaceutically acceptable carrier.

2. The aerosolizer of claim 1 further containing a pharmaceutically acceptable adjuvant.

3. The aerosolizer of claim 2 wherein said pharmaceutically acceptable adjuvant is the B subunit of cholera toxin.

4. The aerosolizer of claim 3 wherein said pneumococcal surface protein A (PspA) is in the form of a killed whole *Streptococcus pneumoniae*.

5. The aerosolizer of claim 3 wherein said pneumococcal surface protein A (PspA) is in the form of a *Streptococcus pneumoniae* lysate.

6. The aerosolizer of claim 3 wherein said pneumococcal surface protein A (PspA) is in the form of an isolated and purified PspA.

7. The aerosolizer of claim 3 wherein said pneumococcal surface protein A (PspA) is in the form of an immunogenic fragment of an isolated and purified PspA, wherein said immunogenic fragment contains a protection-eliciting epitope.

8. A method for inducing an immunological response using said aerosolizer of any one of claims 1, 2, 3, 4, 5, 6, or 7.

* * * * *

SEQUENCE LISTING

<160> NUMBER OF SEQ ID NOS: 4

<210> SEQ ID NO 1
<211> LENGTH: 45
<212> TYPE: PRT
<213> ORGANISM: Streptococcus pneumoniae

<400> SEQUENCE: 1

```
Glu Glu Ser Pro Val Ala Ser Gln Ser Lys Ala Glu Lys Asp Tyr Asp
 1               5                  10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys
        35                  40                  45
```

<210> SEQ ID NO 2
<211> LENGTH: 2086
<212> TYPE: DNA
<213> ORGANISM: Streptococcus pneumoniae

<400> SEQUENCE: 2

```
aagcctatga tatagaaatt tgtaacaaaa atgtaatata aaacacttga caaatattta      60
cggaggaggc ttatacttaa tataagtata gtctgaaaat gactatcaga aaagaggtaa     120
atttagatga ataagaaaaa aatgatttta acaagtctag ccagcgtcgc tatcttaggg     180
gctggttttg ttgcgtctca gcctactgtt gtaagagcag aagaatctcc cgtagccagt     240
cagtctaaag ctgagaaaga ctatgatgca gcgaagaaag atgctaagaa tgcgaaaaaa     300
gcagtagaag atgctcaaaa ggctttagat gatgcaaaag ctgctcagaa aaaatatgac     360
gaggatcaga agaaaactga ggagaaagcc gcgctagaaa aagcagcgtc tgaagagatg     420
gataaggcag tggcagcagt tcaacaagcg tatctagcct atcaacaagc tacagacaaa     480
gccgcaaaag acgcagcaga taagatgata gatgaagcta agaacgcga agaagaggca     540
aaaactaaat ttaatactgt tcgagcaatg gtagttcctg agccagagca gttggctgag     600
actaagaaaa aatcagaaga agctaaacaa aaagcaccag aacttactaa aaaactagaa     660
gaagctaaag caaaattaga agaggctgag aaaaaagcta ctgaagccaa acaaaaagtg     720
gatgctgaag aagtcgctcc tcaagctaaa atcgctgaat tggaaaatca agttcataga     780
ctagaacaag agctcaaaga gattgatgag tctgaatcag aagattatgc taaagaaggt     840
ttccgtgctc ctcttcaatc taaattggat gccaaaaaag ctaaactatc aaaacttgaa     900
gagttaagtg ataagattga tgagttagac gctgaaattg caaaacttga agatcaactt     960
aaagctgctg aagaaaacaa taatgtagaa gactacttta agaaggttt agagaaaact    1020
attgctgcta aaaagctga attagaaaaa actgaagctg accttaagaa agcagttaat    1080
gagccagaaa aaccagctcc agctccagaa actccagccc cagaagcacc agctgaacaa    1140
ccaaaaccag cgccggctcc tcaaccagct cccgcaccaa aaccagagaa gccagctgaa    1200
caaccaaaac cagaaaaaac agatgatcaa caagctgaag aagactatgc tcgtagatca    1260
gaagaagaat ataatcgctt gactcaacag caaccgccaa aagctgaaaa accagctcct    1320
gcaccaaaaa caggctggaa acaagaaaac ggtatgtggt acttctacaa tactgatggt    1380
tcaatggcga caggatggct ccaaaacaac ggttcatggt actacctcaa cagcaatggt    1440
gctatggcta caggttggct ccaatacaat ggttcatggt attacctcaa cgctaacggc    1500
gctatggcaa caggttgggc taaagtcaac ggttcatggt actacctcaa cgctaatggt    1560
gctatggcta caggttggct ccaatacaac ggttcatggt attacctcaa cgctaacggc    1620
gctatggcaa caggttgggc taaagtcaac ggttcatggt actacctcaa cgctaatggt    1680
gctatggcta caggttggct ccaatacaac ggttcatggt actacctcaa cgctaacggt    1740
gctatggcta caggttgggc taaagtcaac ggttcatggt actacctcaa cgctaatggt    1800
gctatggcaa caggttgggt gaaagatgga gatacctggt actatcttga agcatcaggt    1860
gctatgaaag caagccaatg gttcaaagta tcagataaat ggtactatgt caatggttta    1920
ggtgcccttg cagtcaacac aactgtagat ggctataaag tcaatgccaa tggtgaatgg    1980
gtttaagccg attaaattaa agcatgttaa gaacatttga cattttaatt ttgaaacaaa    2040
gataaggttc gattgaatag atttatgttc gtattcttta ggtacc                   2086
```

-continued

<210> SEQ ID NO 3
<211> LENGTH: 648
<212> TYPE: PRT
<213> ORGANISM: Streptococcus pneumoniae

<400> SEQUENCE: 3

Met Asn Lys Lys Met Ile Leu Thr Ser Leu Ala Ser Val Ala Ile
 1               5                  10                  15

Leu Gly Ala Gly Phe Val Ala Ser Gln Pro Thr Val Val Arg Ala Glu
                20                  25                  30

Glu Ser Pro Val Ala Ser Gln Ser Lys Ala Glu Lys Asp Tyr Asp Ala
            35                  40                  45

Ala Lys Lys Asp Ala Lys Asn Ala Lys Lys Ala Val Glu Asp Ala Gln
        50                  55                  60

Lys Ala Leu Asp Asp Ala Lys Ala Ala Gln Lys Lys Tyr Asp Glu Asp
 65                  70                  75                  80

Gln Lys Lys Thr Glu Glu Lys Ala Ala Leu Glu Lys Ala Ala Ser Glu
                 85                  90                  95

Glu Met Asp Lys Ala Val Ala Ala Val Gln Gln Ala Tyr Leu Ala Tyr
                100                 105                 110

Gln Gln Ala Thr Asp Lys Ala Ala Lys Asp Ala Ala Asp Lys Met Ile
            115                 120                 125

Asp Glu Ala Lys Lys Arg Glu Glu Ala Lys Thr Lys Phe Asn Thr
        130                 135                 140

Val Arg Ala Met Val Val Pro Glu Pro Glu Gln Leu Ala Glu Thr Lys
145                 150                 155                 160

Lys Lys Ser Glu Glu Ala Lys Gln Lys Ala Pro Glu Leu Thr Lys Lys
                165                 170                 175

Leu Glu Glu Ala Lys Ala Lys Leu Glu Glu Ala Glu Lys Lys Ala Thr
            180                 185                 190

Glu Ala Lys Gln Lys Val Asp Ala Glu Glu Val Ala Pro Gln Ala Lys
        195                 200                 205

Ile Ala Glu Leu Glu Asn Gln Val His Arg Leu Glu Gln Glu Leu Lys
    210                 215                 220

Glu Ile Asp Glu Ser Glu Ser Glu Asp Tyr Ala Lys Glu Gly Phe Arg
225                 230                 235                 240

Ala Pro Leu Gln Ser Lys Leu Asp Ala Lys Lys Ala Lys Leu Ser Lys
                245                 250                 255

Leu Glu Glu Leu Ser Asp Lys Ile Asp Glu Leu Asp Ala Glu Ile Ala
            260                 265                 270

Lys Leu Glu Asp Gln Leu Lys Ala Ala Glu Glu Asn Asn Asn Val Glu
        275                 280                 285

Asp Tyr Phe Lys Glu Gly Leu Glu Lys Thr Ile Ala Ala Lys Lys Ala
    290                 295                 300

Glu Leu Glu Lys Thr Glu Ala Asp Leu Lys Lys Ala Val Asn Glu Pro
305                 310                 315                 320

Glu Lys Pro Ala Pro Ala Pro Glu Thr Pro Ala Pro Glu Ala Pro Ala
                325                 330                 335

Glu Gln Pro Lys Pro Ala Pro Ala Pro Gln Pro Ala Pro Ala Pro Lys
            340                 345                 350

Pro Glu Lys Pro Ala Glu Gln Pro Lys Pro Glu Lys Thr Asp Asp Gln
        355                 360                 365

Gln Ala Glu Glu Asp Tyr Ala Arg Arg Ser Glu Glu Glu Tyr Asn Arg
    370                 375                 380

-continued

```
Leu Thr Gln Gln Gln Pro Pro Lys Ala Glu Lys Pro Ala Pro Ala Pro
385                 390                 395                 400

Lys Thr Gly Trp Lys Gln Glu Asn Gly Met Trp Tyr Phe Tyr Asn Thr
            405                 410                 415

Asp Gly Ser Met Ala Thr Gly Trp Leu Gln Asn Asn Gly Ser Trp Tyr
        420                 425                 430

Tyr Leu Asn Ser Asn Gly Ala Met Ala Thr Gly Trp Leu Gln Tyr Asn
    435                 440                 445

Gly Ser Trp Tyr Tyr Leu Asn Ala Asn Gly Ala Met Ala Thr Gly Trp
450                 455                 460

Ala Lys Val Asn Gly Ser Trp Tyr Tyr Leu Asn Ala Asn Gly Ala Met
465                 470                 475                 480

Ala Thr Gly Trp Leu Gln Tyr Asn Gly Ser Trp Tyr Tyr Leu Asn Ala
            485                 490                 495

Asn Gly Ala Met Ala Thr Gly Trp Ala Lys Val Asn Gly Ser Trp Tyr
        500                 505                 510

Tyr Leu Asn Ala Asn Gly Ala Met Ala Thr Gly Trp Leu Gln Tyr Asn
    515                 520                 525

Gly Ser Trp Tyr Tyr Leu Asn Ala Asn Gly Ala Met Ala Thr Gly Trp
530                 535                 540

Ala Lys Val Asn Gly Ser Trp Tyr Tyr Leu Asn Ala Asn Gly Ala Met
545                 550                 555                 560

Ala Thr Gly Trp Val Lys Asp Gly Asp Thr Trp Tyr Tyr Leu Glu Ala
            565                 570                 575

Ser Gly Ala Met Lys Ala Ser Gln Trp Phe Lys Val Ser Asp Lys Trp
        580                 585                 590

Tyr Tyr Val Asn Gly Leu Gly Ala Leu Ala Val Asn Thr Thr Val Asp
    595                 600                 605

Gly Tyr Lys Val Asn Ala Asn Gly Glu Trp Val Ala Asp Ile Lys Ala
610                 615                 620

Cys Glu His Leu Thr Phe Phe Asn Lys Asp Lys Val Arg Leu Asn Arg
625                 630                 635                 640

Phe Met Phe Val Phe Phe Tyr Tyr
                645

<210> SEQ ID NO 4
<211> LENGTH: 288
<212> TYPE: PRT
<213> ORGANISM: Streptococcus pneumoniae

<400> SEQUENCE: 4

Glu Glu Ser Pro Val Ala Ser Gln Ser Lys Ala Glu Lys Asp Tyr Asp
 1               5                  10                  15

Ala Ala Lys Lys Asp Ala Lys Asn Ala Lys Lys Ala Val Glu Asp Ala
            20                  25                  30

Gln Lys Ala Leu Asp Asp Ala Lys Ala Ala Gln Lys Lys Tyr Asp Glu
        35                  40                  45

Asp Gln Lys Lys Thr Glu Glu Lys Ala Ala Leu Glu Lys Ala Ala Ser
    50                  55                  60

Glu Glu Met Asp Lys Ala Val Ala Ala Val Gln Gln Ala Tyr Leu Ala
65                  70                  75                  80

Tyr Gln Gln Ala Thr Asp Lys Ala Ala Lys Asp Ala Ala Asp Lys Met
            85                  90                  95

Ile Asp Glu Ala Lys Lys Arg Glu Glu Glu Ala Lys Thr Lys Phe Asn
```

-continued

```
                    100                 105                 110
Thr Val Arg Ala Met Val Val Pro Glu Pro Glu Gln Leu Ala Glu Thr
        115                 120                 125
Lys Lys Lys Ser Glu Glu Ala Lys Gln Lys Ala Pro Glu Leu Thr Lys
        130                 135                 140
Lys Leu Glu Glu Ala Lys Ala Lys Leu Glu Glu Ala Glu Lys Lys Ala
145                 150                 155                 160
Thr Glu Ala Lys Gln Lys Val Asp Ala Glu Glu Val Ala Pro Gln Ala
                165                 170                 175
Lys Ile Ala Glu Leu Glu Asn Gln Val His Arg Leu Glu Gln Glu Leu
                180                 185                 190
Lys Glu Ile Asp Glu Ser Glu Ser Glu Asp Tyr Ala Lys Glu Gly Phe
        195                 200                 205
Arg Ala Pro Leu Gln Ser Lys Leu Asp Ala Lys Lys Ala Lys Leu Ser
        210                 215                 220
Lys Leu Glu Glu Leu Ser Asp Lys Ile Asp Glu Leu Asp Ala Glu Ile
225                 230                 235                 240
Ala Lys Leu Glu Asp Gln Leu Lys Ala Ala Glu Glu Asn Asn Asn Val
                245                 250                 255
Glu Asp Tyr Phe Lys Glu Gly Leu Glu Lys Thr Ile Ala Ala Lys Lys
                260                 265                 270
Ala Glu Leu Glu Lys Thr Glu Ala Asp Leu Lys Lys Ala Val Asn Glu
        275                 280                 285
```